(12) United States Patent
Kirschhoffer et al.

(10) Patent No.: US 10,363,557 B2
(45) Date of Patent: Jul. 30, 2019

(54) APPARATUS AND METHOD FOR PREPARING A BIOLOGICAL SAMPLE FOR ANALYSIS

(71) Applicant: 3M INNOVATIVE PROPERTIES COMPANY, St. Paul, MN (US)

(72) Inventors: Jon A. Kirschhoffer, Stillwater, MN (US); Gregory W. Sitton, Minneapolis, MN (US); Andrew H. Tilstra, Shoreview, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 16/124,715

(22) Filed: Sep. 7, 2018

(65) Prior Publication Data

US 2019/0001321 A1 Jan. 3, 2019

Related U.S. Application Data

(62) Division of application No. 15/100,806, filed as application No. PCT/US2014/068999 on Dec. 8, 2014, now Pat. No. 10,099,217.

(60) Provisional application No. 61/915,124, filed on Dec. 12, 2013.

(51) Int. Cl.
*B01L 3/00* (2006.01)
*C12Q 1/24* (2006.01)

(52) U.S. Cl.
CPC ............ *B01L 3/502* (2013.01); *C12Q 1/24* (2013.01); *B01L 2200/0689* (2013.01); *B01L 2300/0681* (2013.01); *B01L 2300/087* (2013.01); *B01L 2300/0832* (2013.01); *B01L 2300/123* (2013.01); *B01L 2400/0478* (2013.01); *B01L 2400/0605* (2013.01); *B01L 2400/0611* (2013.01)

(58) Field of Classification Search
CPC combination set(s) only.
See application file for complete search history.

(56) References Cited

U.S. PATENT DOCUMENTS

| 3,282,224 | A | 11/1966 | Bock et al. |
| 4,908,319 | A | 3/1990 | Smyczek et al. |
| 5,085,562 | A | 2/1992 | Van Lintel |
| 5,786,182 | A | 7/1998 | Cantanzariti |
| 5,989,499 | A | 11/1999 | Cantanzariti |
| 7,977,089 | B2 | 7/2011 | Wikswo et al. |

(Continued)

FOREIGN PATENT DOCUMENTS

| JP | 2006-508343 | 3/2006 |
| WO | WO 2004/047992 | 6/2004 |

OTHER PUBLICATIONS

Berry, E.D. et al.; "Hydroxyapatite Adherence as a Means to Concentrate Bacteria"; Applied and Environmental Microbiology; vol. 63. No. 10; 1997; pp. 4069-4074.

(Continued)

*Primary Examiner* — Brian R Gordon
(74) *Attorney, Agent, or Firm* — Eric E. Silverman

(57) ABSTRACT

An apparatus for processing a biological sample is provided. The apparatus has a body having a processing chamber, a first reservoir, a second reservoir, a filter, a first one-way valve, a second one-way valve, a third one-way valve, a first fluid pathway, a second fluid pathway, and a third fluid pathway.

8 Claims, 12 Drawing Sheets

(56) References Cited

U.S. PATENT DOCUMENTS

| | | |
|---|---|---|
| 8,313,906 B2 | 11/2012 | Cao et al. |
| 2003/0162304 A1 | 8/2003 | Dority et al. |
| 2004/0120836 A1 | 6/2004 | Dai et al. |
| 2004/0182795 A1 | 9/2004 | Dorian et al. |
| 2006/0011539 A1 | 1/2006 | Lee et al. |
| 2010/0041131 A1* | 2/2010 | Brown .............. B01L 3/0206 435/309.1 |
| 2010/0062421 A1 | 3/2010 | Xia et al. |
| 2012/0288897 A1 | 11/2012 | Ching et al. |
| 2013/0273548 A1 | 10/2013 | Mastromatteo et al. |

OTHER PUBLICATIONS

Oster, J. et al.; "Polyvinyl-alcohol-based magnetic beads for rapid and efficient separation of specific or unspecific nucleic acid sequences"; Journal of Magnetism and Magnetic Materials; vol. 225; 2001; pp. 145-150.

* cited by examiner

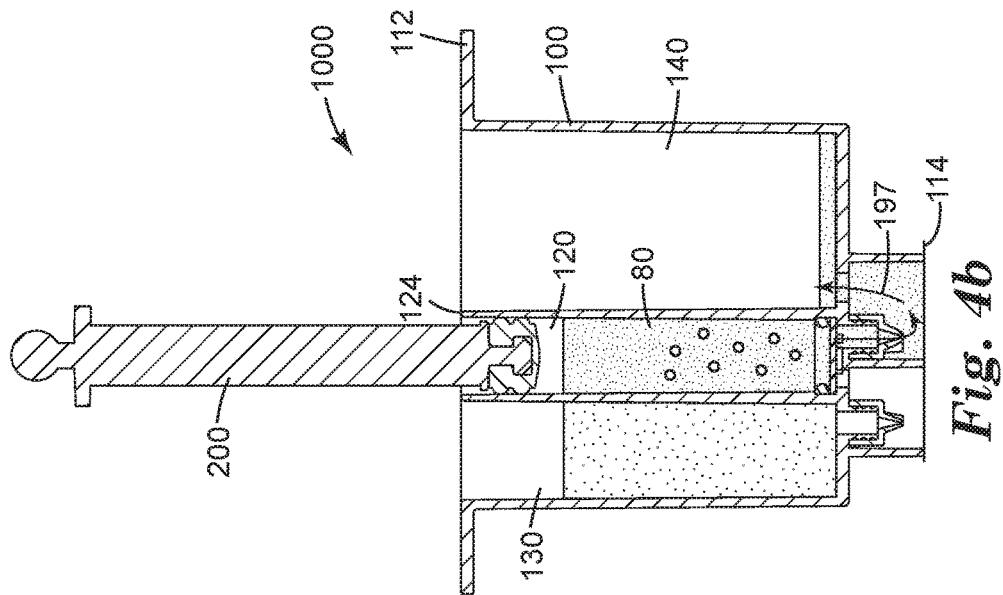
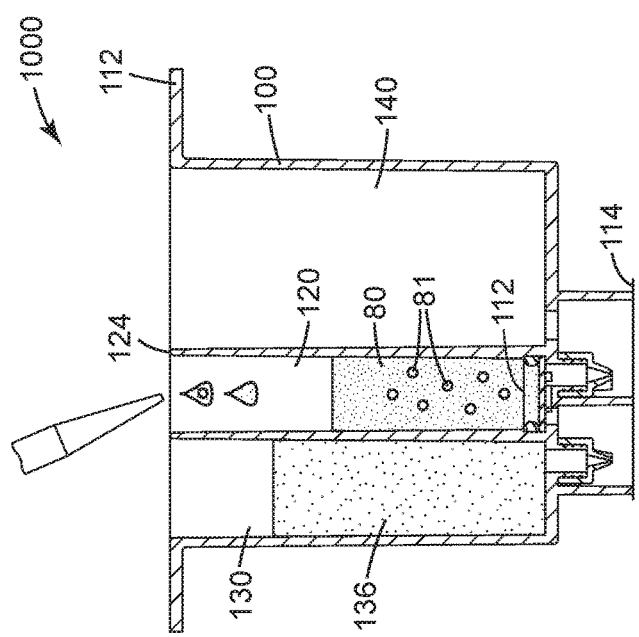

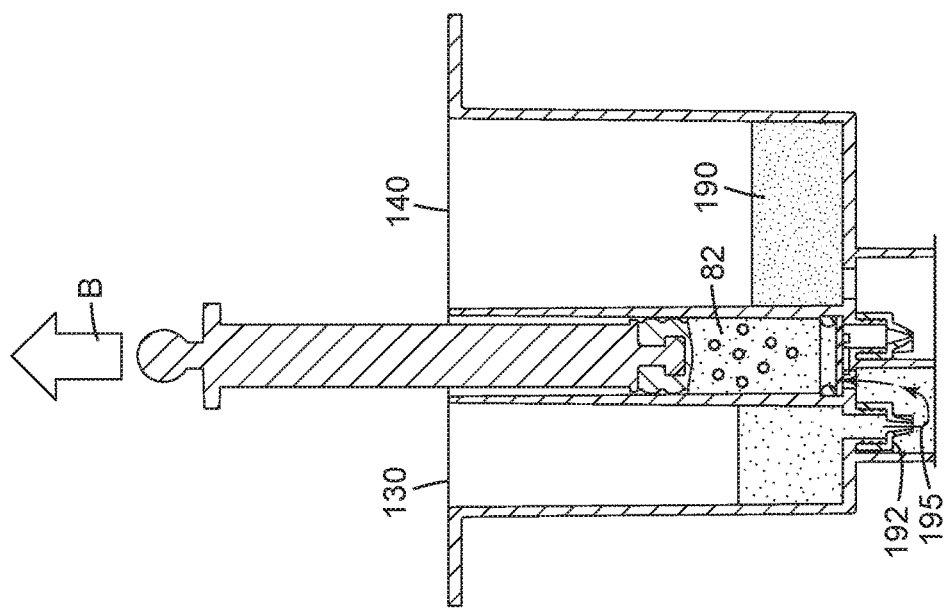
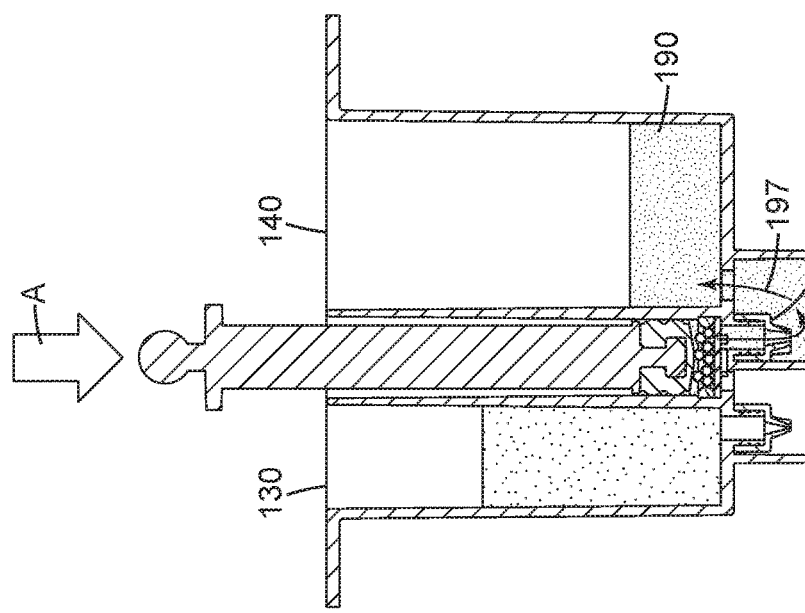

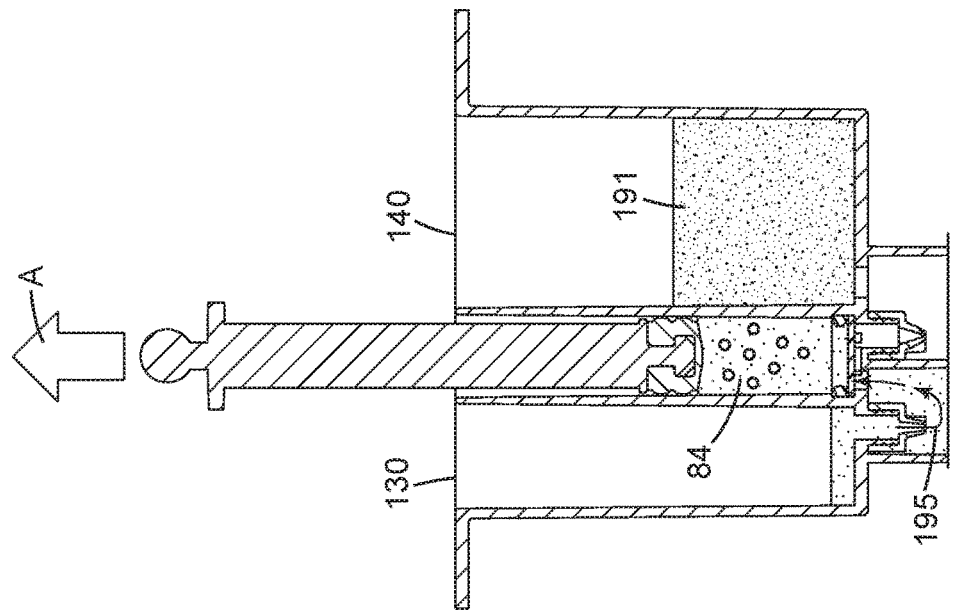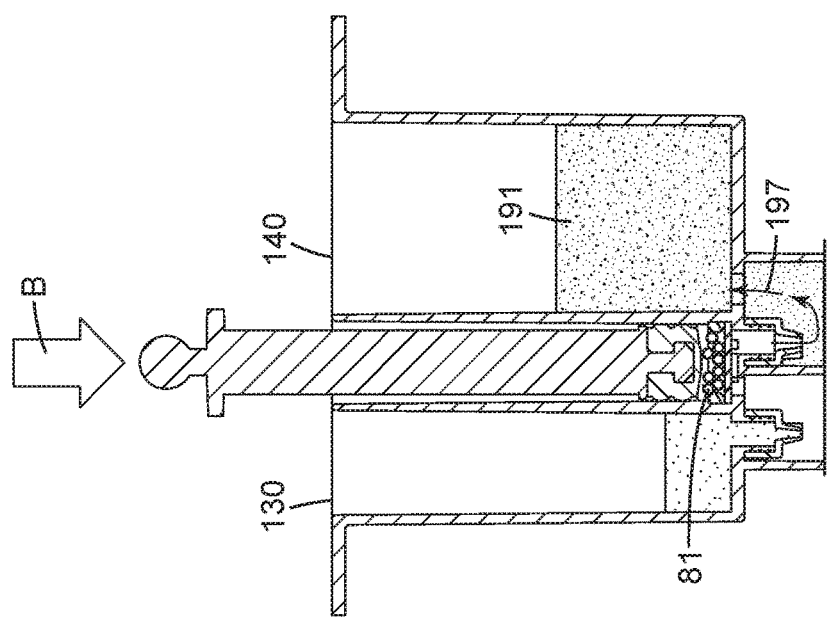

APPARATUS AND METHOD FOR PREPARING A BIOLOGICAL SAMPLE FOR ANALYSIS

CROSS REFERENCE TO RELATED APPLICATIONS

This application is a divisional of U.S. application Ser. No. 15/100,806, filed Jun. 1, 2016, now pending, which is a 35 U.S.C. 371 of PCT/US2014/068999, filed Dec. 8, 2014, which claims priority to U.S. Provisional Application No. 61/915,124, filed Dec. 12, 2013.

BACKGROUND

Many types of samples (e.g., clinical, environmental, food, and beverage samples) are routinely tested for the presence or absence of microorganisms. In particular many samples are tested for the presence of pathogenic microorganisms. Often, the samples require various types of pre-treatment (i.e., processing prior to a detection step) in order to increase the number of target microorganisms, decrease, the number of non-target microorganisms, concentrate the microorganisms, and/or reduce the quantity of potentially-interfering material in the sample. The pre-treatment steps may be laborious and can take several hours to several days to complete. A variety of materials and devices have been developed to reduce the number of steps and the time that it takes to complete the pre-treatment of samples.

Processing a plurality of samples simultaneously can be difficult because of the lack of simple, efficient devices for the procedure. There remains a need for simple, methods to prepare one or more samples for the detection of microorganisms.

SUMMARY

The present disclosure is directed to the detection of a microorganism in a sample. In particular, the present disclosure provides an apparatus and a corresponding method of use for processing a sample to detect the presence or absence of an analyte associated with a microorganism. Advantageously, the apparatus is configured such that it can reduce the amount of interfering material in the sample, concentrate the analyte, and can be used to hold the sample at an elevated temperature in order to lyse microorganism cells and release the analyte. Optionally, the concentrated analyte subsequently be transferred to a container for detection of the analyte.

In one aspect, the present disclosure provides an apparatus. The apparatus can comprise a body having a first end and a second end opposite the first end. The body can comprise a processing chamber, a first reservoir, a second reservoir, a filter, a first one-way valve, and a second one-way valve. The processing chamber can comprise an opening proximate the first end. The first reservoir can be disposed in selective fluid communication with the processing chamber via a first fluid pathway. The second reservoir can be disposed in selective fluid communication with the processing chamber via a second fluid pathway. The first fluid pathway and the second fluid pathway can pass through the filter. The filter can have a first side oriented in the fluid pathways toward the processing chamber and a second side opposite the first side. The first one-way valve can be disposed in the first fluid pathway between the filter and the first reservoir and can provide selective fluid communication between the processing chamber and the first reservoir. The second one-way valve can be disposed in the second fluid pathway between the filter and the second reservoir and can provide selective fluid communication between the processing chamber and the second reservoir.

In another aspect, the present disclosure provides a method of processing a sample. The method can comprise placing a sample comprising a liquid into a processing chamber of an apparatus. The apparatus can comprise a body having a first end and a second end opposite the first end. The body can comprise the processing chamber, a first reservoir, a second reservoir, a filter, a first one-way valve, and a second one-way valve. The processing chamber can comprise an opening proximate the first end. The first reservoir can be disposed in selective fluid communication with the processing chamber via a first fluid pathway. The second reservoir can be disposed in selective fluid communication with the processing chamber via a second fluid pathway. The first fluid pathway and the second fluid pathway can pass through the filter. The filter can have a first side oriented in the fluid pathways toward the processing chamber and a second side opposite the first side. The first one-way valve can be disposed in the first fluid pathway between the filter and the first reservoir and can provide selective fluid communication between the processing chamber and the first reservoir. The second one-way valve can be disposed in the second fluid pathway between the filter and the second reservoir and can provide selective fluid communication between the processing chamber and the second reservoir. The method further can comprise urging at least a portion of the liquid out of the processing chamber through the filter; after urging the at least a portion of the liquid through the filter, urging a first portion of a back-flush liquid from the first reservoir through the filter and into the process chamber to form a first processed sample; and analyzing at least a portion of the sample to detect an indication of a microorganism, wherein analyzing at least a portion of the sample comprises analyzing at least a portion of the first processed sample.

In yet another aspect, the present disclosure provides an apparatus. The apparatus can comprise a body having a first end and a second end opposite the first end. The body can comprise a plurality of liquid-sample processing modules including a first module and a second module. Each module of the plurality of modules can comprise a processing chamber, a first reservoir, a second reservoir, a filter, a first one-way valve, and a second one-way valve. The processing chamber can comprise an opening proximate the first end. The first reservoir can be disposed in selective fluid communication with the processing chamber via a first fluid pathway. The second reservoir can be disposed in selective fluid communication with the processing chamber via a second fluid pathway. The first fluid pathway and the second fluid pathway can pass through the filter. The filter can have a first side oriented in the fluid pathways toward the processing chamber and a second side opposite the first side. The first one-way valve can be disposed in the first fluid pathway between the filter and the first reservoir and can provide selective fluid communication between the processing chamber and the first reservoir. The second one-way valve can be disposed in the second fluid pathway between the filter and the second reservoir and can provide selective fluid communication between the processing chamber and the second reservoir. The first module can be coupled to the second module.

In yet another aspect, the present disclosure provides an apparatus. The apparatus can comprise a body having a first end and a second end opposite the first end. The body can comprise a plurality of processing chambers. The plurality can comprise plurality processing chambers comprising a first processing chamber and a second processing chamber. Each processing chamber can comprise an opening proximate the first end. The apparatus further can comprise a first reservoir, a second reservoir, a first filter, a second filter, a first one-way valve, a second one-way valve, and a third one-way valve. The first reservoir can be disposed in selective fluid communication with the first processing chamber via a first fluid pathway. The second reservoir can be disposed in selective fluid communication with the first processing chamber via a second fluid pathway and in selective fluid communication with the second processing chamber via a third fluid pathway. The first filter can be disposed in the body between at least a portion of the first processing chamber and the second reservoir. The first fluid pathway and the second fluid pathway can pass through the first filter. The first filter can have a first surface oriented in the first and second fluid pathways toward the first processing chamber. The second filter can be disposed in the body between at least a portion of the second processing chamber and the second reservoir. The third fluid pathway can pass through the second filter. The second filter can have a first surface oriented in the third fluid pathway toward the second processing chamber. The first one-way valve can be disposed in the first fluid pathway between the first filter and the first reservoir and can provide selective fluid communication between the first processing chamber and the first reservoir. The second one-way valve can be disposed in the second fluid pathway between the first filter and the second reservoir and can provide selective fluid communication between the first processing chamber and the second reservoir. The third one-way valve can be disposed in the third fluid pathway between the second filter and the first reservoir and can provide selective fluid communication between the second processing chamber and the first reservoir.

In yet another aspect, the present disclosure provides a kit. The kit can comprise an apparatus. The apparatus can comprise a body having a first end and a second end opposite the first end. The body can comprise a processing chamber, a first reservoir, a second reservoir, a filter, a first one-way valve, and a second one-way valve. The processing chamber can comprise an opening proximate the first end. The first reservoir can be disposed in selective fluid communication with the processing chamber via a first fluid pathway. The second reservoir can be disposed in selective fluid communication with the processing chamber via a second fluid pathway. The first fluid pathway and the second fluid pathway can pass through the filter. The filter can have a first side oriented in the fluid pathways toward the processing chamber and a second side opposite the first side. The first one-way valve can be disposed in the first fluid pathway between the filter and the first reservoir and can provide selective fluid communication between the processing chamber and the first reservoir. The second one-way valve can be disposed in the second fluid pathway between the filter and the second reservoir and can provide selective fluid communication between the processing chamber and the second reservoir.

In any embodiment, the kit further can comprise a reagent selected from the group consisting of a sample resuspension liquid, a cell-lysis reagent, a reagent used in a nucleic acid amplification reaction, and a reagent used in an antigen detection reaction. In any embodiment, the kit further can comprise a prefilter and/or a culture device.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

As used herein, "a," "an," "the," "at least one," and "one or more" are used interchangeably. Thus, for example, "a" chamber can be interpreted to mean "one or more" chambers.

The term "and/or" means one or all of the listed elements or a combination of any two or more of the listed elements.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

Additional details of these and other embodiments are set forth in the accompanying drawings and the description below. Other features, objects and advantages will become apparent from the description and drawings, and from the claims.

BRIEF DESCRIPTION OF DRAWINGS

FIGS. 4a-4f depict a series of cross-sectional views of the apparatus of FIG. 1 showing steps in one embodiment of a method of processing a sample according to the present disclosure.

Figure 1:
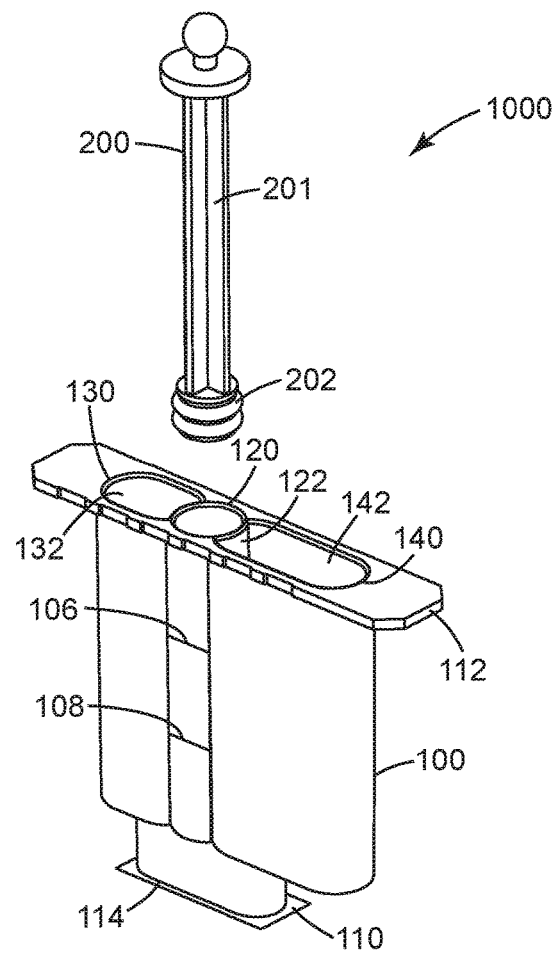
FIG. 1 is a partially-exploded, top perspective view of one embodiment of a sample-processing apparatus comprising a body, the body having a first end and a second end according to the present disclosure.

While the above-identified drawing figures set forth several embodiments of the disclosure, other embodiments are also contemplated, as noted in the discussion. In all cases, this disclosure presents the invention by way of representation and not limitation. It should be understood that numerous other modifications and embodiments can be devised by those skilled in the art, which fall within the scope and spirit of the principles of the invention. The figures may not be drawn to scale.

DETAILED DESCRIPTION

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "connected" and "coupled" and variations thereof are used broadly and encompass both direct and indirect connections and couplings. Further, "connected" and "coupled" are not restricted to physical or mechanical connections or couplings. It is to be understood that other embodiments may be utilized and structural or logical changes may be made without departing from the scope of the present disclosure. Furthermore, terms such as "front," "rear," "top," "bottom," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

The present disclosure generally relates to the detection of an analyte in a sample. In particular, the inventive apparatus and method can be used to detect a biological cell, or a component thereof, present in a sample. In any embodiment, the apparatus and method are used to detect an analyte (e.g., a protein, an antigen, a polynucleotide) associated with a microorganism cell (e.g., a bacterium, a yeast cell, a fungal cell). A person having ordinary skill in the art will also recognize the apparatus and method may be useful for isolating, purifying and, optionally concentrating particulate non-biological analytes.

In particular, the present disclosure generally relates to preparing a sample to detect the presence or absence of an analyte. In particular, the present disclosure provides an apparatus and a method to facilitate the removal of potentially-interfering material (e.g., metal ions, hydronium ions, hydroxide ions, biomolecules such as lipids, proteins, and nucleic acids, for example) from a liquid sample and to capture the analyte for subsequent analysis. In addition, in any embodiment, the apparatus and method can be used to concentrate the analyte in order to provide faster and/or more-sensitive detection of the analyte.

Advantageously, the resulting captured analyte is relatively free of impurities and is suitable for use in a variety of detection methods (e.g., immunodetection methods and nucleic acid detection methods). When the detection method includes lysing cells (e.g., using heat and/or chemical lysing agents) in order to detect an intracellular analyte (e.g., a protein or nucleic acid), the sample can be lysed directly in the inventive apparatus prior to subsequent detection steps.

The present disclosure includes methods and an apparatus for processing a single sample. The present disclosure further includes a method and an apparatus for processing, either simultaneously or sequentially, a plurality of samples.

The sample can be any sample comprising or suspected of comprising an analyte (e.g., a biological analyte) capable of being detected. Nonlimiting examples of suitable samples include suspensions or cultures of cells (e.g., mammalian cells, insect cells, yeast cells, filamentous fungi, bacterial cells), environmental samples (e.g., surface swabs), food (e.g., raw materials, in-process samples, and finished-product samples), beverages, clinical samples (e.g., blood, urine, sputum, tissue, mucous, feces, wound exudate, pus), and water (e.g., surface water, potable water, process water).

Non-limiting examples of suitable biological analytes include nucleic acids (e.g., a polynucleotide associated with a particular type of cell or microorganism) or detectable antigens (e.g., proteins, oligopeptides, enzymes, endotoxin, cell membrane components, and cell wall components). Analytical procedures to detect the biological analytes are known in the art. Preferred biological analytes to be detected include nucleic acids that are capable of being amplified in a reaction (e.g., PCR), for example.

In any embodiment, the sample comprises a liquid (e.g., an aqueous liquid). Besides liquid samples, other test samples may include liquids as well as solid(s) dissolved or suspended in a liquid medium. Samples of interest may include process streams, water, soil, plants or other vegetation, air, surfaces (e.g., contaminated surfaces), and the like. Samples can also include cultured cells. Samples can also include samples from a surface of and/or contents of a culture device comprising cells, spores, or enzymes (e.g., a biological indicator device).

Solid samples may be also be used in the apparatus and methods of the present disclosure. For example, the solid sample can be disintegrated (e.g., by blending, sonication, homogenization) and/or suspended in a liquid (e.g., water, buffer, broth) before placing the sample into the apparatus of the present disclosure. Alternatively, the solid sample may be disintegrated and/or suspended in a liquid in the apparatus of the present disclosure. In any embodiment, a sample-collection device (e.g., a swab, a sponge) containing sample material may be used in the method. Alternatively, the sample material may be eluted (e.g., rinsed, scraped, expressed) from the sample-collection device before using the sample material in the method. In some embodiments, liquid or solid samples may be diluted in a liquid (e.g., water, buffer, broth).

Suitable samples also include cell-suspension media (e.g., culture broth, semi-solid cell culture media, and tissue culture media, filtrate) that contain cells or previously contained cells. Suitable samples also include cell lysates. Cell lysates may be produced by chemical means (e.g., detergents, enzymes), mechanical means (sonic vibration, homogenization, French Press), or by other cell lytic means known in the art.

Microorganisms (e.g., bacteria, fungi, viruses) are a source of detectable analytes. Microorganisms can be analyzed in a test sample that may be derived from a variety of sources, as described herein. Microorganisms of particular interest include prokaryotic and eukaryotic organisms, particularly Gram positive bacteria, Gram negative bacteria, fungi, protozoa, mycoplasma, yeast, viruses, and even lipid-enveloped viruses. Particularly relevant organisms include members of the family Enterobacteriaceae, or the family Micrococcaceae or the genera *Staphylococcus* spp., *Streptococcus* spp., *Pseudomonas* spp., *Enterococcus* spp., *Salmonella* spp., *Legionella* spp., *Shigella* spp. *Yersinia* spp., *Enterobacter* spp., *Escherichia* spp., *Bacillus* spp., *Listeria* spp., *Vibrio* spp., Corynebacteria spp. as well as herpes virus, *Aspergillus* spp., *Fusarium* spp., and *Candida* spp. Particularly virulent organisms include *Staphylococcus aureus* (including resistant strains such as Methicillin Resistant *Staphylococcus aureus* (MRSA)), *S. epidermidis*, *Streptococcus pneumoniae*, *S. agalactiae*, *S. pyogenes*, *Enterococcus faecalis*, Vancomycin Resistant *Enterococcus* (VRE), Vancomycin Resistant *Staphylococcus aureus* (VRSA), Vancomycin Intermediate-resistant *Staphylococcus aureus* (VISA), *Bacillus anthracis*, *Pseudomonas aeruginosa*, *Escherichia coli*, *Aspergillus niger*, *A. fumigatus*, *A. clavatus*, *Fusarium solani*, *F. oxysporum*, *F. chlamydosporum*, *Listeria monocytogenes*, *Listeria ivanovii*, *Vibrio cholera*, *V parahaemolyticus*, *Salmonella choleraesuis*, *S. typhi*, *S. typhimurium*, *Candida albicans*, *C. glabrata*, *C. krusei*, *Enterobacter sakazakii*, *E. coli* O157 and multiple drug resistant Gram negative rods (MDR).

Gram positive and Gram negative bacteria are of particular interest. Of even more interest are Gram positive bacteria, such as *Staphylococcus aureus*. Also, of particular interest are antibiotic resistant microbes including MRSA, VRSA, VISA, VRE, and MDR.

Figure 2:
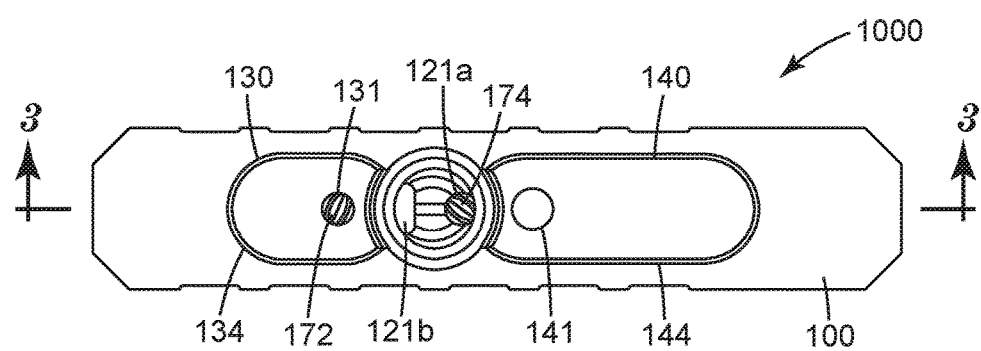
FIG. 2 is a top view of the sample-processing apparatus of FIG. 1, with the filter removed in order to show openings, proximate the second end of the body, in a processing chamber and in first and second reservoirs.
Figure 3:
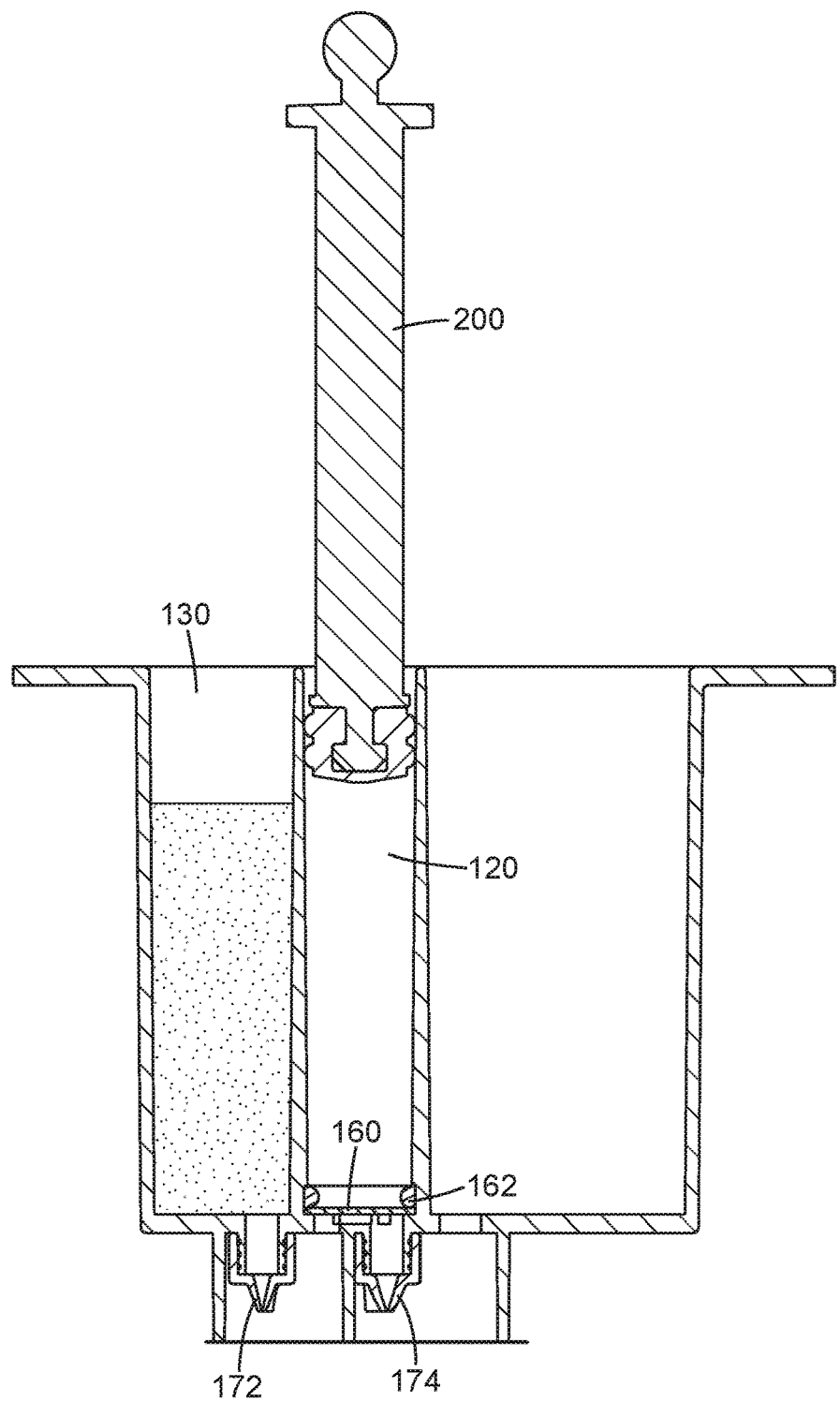
FIG. 3 is a cross-sectional view of the sample-processing apparatus of FIG. 2, taken along line 3-3.

Turning now to the drawings, FIGS. 1-3 depict several views of a sample-processing apparatus 1000 according to the present disclosure. The apparatus 1000 comprises a body 100 and, optionally, a plunger 200. The body 100 comprises a first end 112 and a second end 114 opposite the first end. The body 100 further comprises a processing chamber 120, a first reservoir 130, and a second reservoir 140. The optional plunger 200 comprises a stem portion 201 and sealing member 202. In any embodiment of an apparatus of the present disclosure, the second end 114 of the body 100 optionally comprises a securement means 118 (e.g., double-sided adhesive tape) for securing the apparatus 1000 to a substrate (not shown).

The body 100 and at least a portion (e.g., the stem portion 201) of the plunger 200 can be fabricated using materials and processes that are known in the art. For example, the body 100 and plunger 200 may be made by conventional molding processes using a suitable polymeric material (e.g., polyethylene, polypropylene, polystyrene, polycarbonate, Acrylonitrile Butadiene Styrene (ABS) plastic). In any embodiment, the material from which the body 100 is made is optically transmissible (i.e., the material is transparent or translucent. Advantageously, this permits the operator using the apparatus 1000 to observe, for example, the status of the plunger 200 or a liquid level (e.g., a sample liquid, a liquid in the first reservoir 130 and/or second reservoir 140) as the apparatus 1000 is being used.

Optionally, in any embodiment, the sealing member 202 can be made from a more-conformable material (e.g., butyl rubber, silicone rubber, oil-impregnated silicone rubber) using conventional processes (e.g., molding processes) that are known in the art. In these embodiments, the sealing member 202 is coupled to the stem portion 201 using any one of a variety of means (e.g., press-fit, adhesive means such as a pressure-sensitive adhesive, an ultrasonic weld). In any embodiment, the sealing member can be molded onto the stem portion using "2-shot" molding processes that are known in the art. In any embodiment, the stem and the sealing member of the plunger can be made from a single material that is sufficiently compliant to form a liquid-tight seal when the plunger is inserted into the body of the apparatus.

The processing chamber 120 has an opening 124 proximate the first end 112 of the body 100. The opening 124 is configured (e.g., shaped and dimensioned) to receive at least a portion of the plunger 200.

The processing chamber 120, the first reservoir 130, and the second reservoir 140 comprise at least one wall that defines the shape and inner volume of the respective structure. A person having ordinary skill in the art in view of the present disclosure will recognize the processing chamber, the first reservoir, and the second reservoir can define a variety of shapes and sizes that are suitable for use as described herein. For example, the processing chamber 120 of the illustrated embodiment of FIGS. 1-3 comprises a wall 122 that defines a cylindrically-shaped processing chamber. The first reservoir 130 is defined in part by walls 122 and 132, respectively. The second reservoir 140 is defined in part by walls 122 and 142, respectively. Thus, in any embodiment, the first reservoir 130 and/or the second reservoir 140 is immediately adjacent the processing chamber 120. Advantageously, this configuration (i.e., the reservoirs immediately adjacent the processing chamber) affords a substantially compact design. Although the reservoirs (first reservoir 130 and second reservoir 140) and processing chamber 120 are shown in a substantially linear array, other arrangements (e.g., with the reservoirs and process chamber forming a triangular arrangement, not shown) are contemplated.

The at least one wall (e.g., wall 122) of the processing chamber 120 and, in the illustrated embodiment, a filter 160 (described below) define a first operational volume (e.g., the inner volume of the processing chamber). The first operational volume can be selected from a variety of volumes that are suitable for processing typical samples. In any embodiment, the first operational volume is at least about 0.02 mL to about 100 mL. In any embodiment, the first operational volume is at least about 0.02 mL to about 25 mL. In any embodiment, the first operational volume is at least about 0.02 mL to about 10 mL. In any embodiment, the first operational volume is about 1 mL to about 100 mL. In any embodiment, the first operational volume is 1 mL to about 5 mL.

In any embodiment, the body 100 of the apparatus 1000 further comprises a visual indicium to indicate a predetermined volume. In any embodiment, the body 100 may comprise a plurality of visual indicia. FIG. 1 shows a body 100 comprising two visual indicia (i.e., first visual indicium 106 and second visual indicium 108) that indicate a first predetermined volume and second predetermined volume, respectively, of the processing chamber 120. Typically, the visual indicia are used by placing the apparatus 1000 on a relatively flat, level surface and determining visually whether the meniscus of a liquid (not shown in FIG. 1) present in the apparatus 1000 is approximately level with one of the indicia (i.e., first visual indicium 106 or second visual indicium 108), indicating that a part of the body (e.g., the processing chamber 120) is holding the predetermined volume of liquid. Both visual indicia in the illustrated embodiment indicate predetermined volumes of the processing chamber 120. In any embodiment, the ratio of the first predetermined volume to the second predetermined volume may define an operational concentration ratio. In any embodiment, the ratio of a first predetermined volume of the processing chamber to a second predetermined volume may be about 2:1, about 3:1, about 4:1, about 5:1, about 10:1, about 20:1, about 50:1, or about 100:1.

Alternatively or additionally, in any embodiment, the body may comprise a visible indicium (not shown) indicating a predetermined volume of the first reservoir and/or a visible indicium (not shown) indicating a predetermined volume of the second reservoir. In any embodiment, the body may comprise a plurality of visual indicia that indicate first and second predetermined volumes of the first reservoir and/or second reservoir. Advantageously, a first visible indicium denoting a first predetermined volume of the first reservoir can be used to indicate, for example, a fill volume for a wash liquid (e.g., water, a buffer) deposited into the first reservoir and a second visible indicium denoting a second predetermined volume can be used to indicate a proper volume of wash liquid has been transferred from the first reservoir into the processing chamber, as described below. Advantageously, a visible indicium denoting a predetermined volume of the second reservoir can be used to indicate a sample being processed in the processing chamber has been washed with a proper volume of liquid and/or has been sufficiently concentrated and is ready for further processing, as described below.

The wall 122 of the processing chamber 120 and at least a portion (e.g., the stem portion 201 and the sealing member 202) of the plunger 200 are configured so that at least part of the plunger can be removably inserted into the processing chamber and can slideably traverse through at least a portion of the processing chamber. Preferably, a portion (e.g., the sealing member 202) of the plunger 200 forms a substantially fluid-tight fit when engaged with the wall 122 in the processing chamber 120, thereby facilitating the establishment of positive or negative pressure in the processing chamber when the plunger is inserted in the processing chamber and urged toward the second end 114 or first end 112 of the body 100.

Figure 3A:
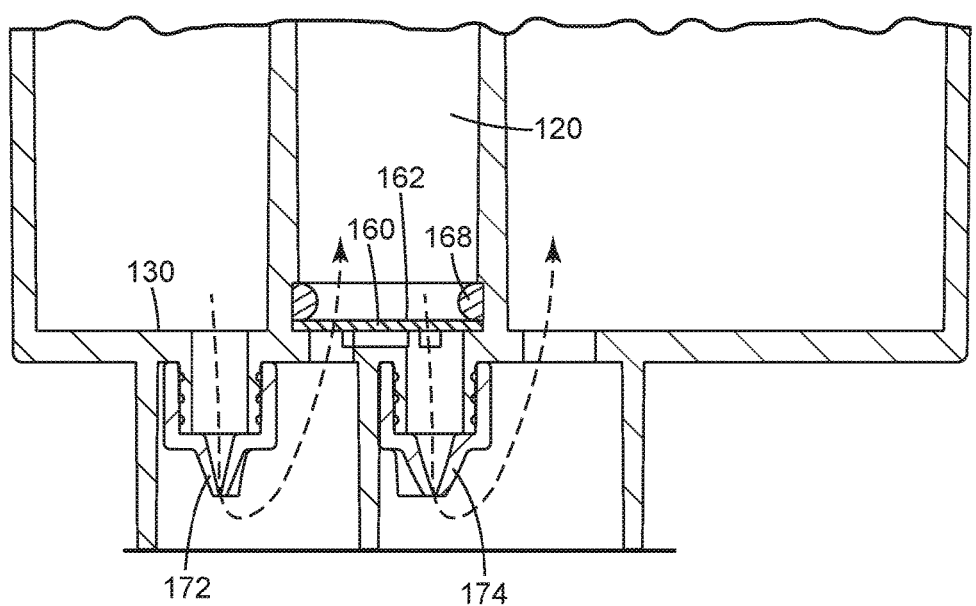
FIG. 3a is a detailed view of the second end of the sample-processing apparatus of FIG. 3.

The first reservoir 130 is in fluid communication with the processing chamber 120. FIG. 3a shows a detail view of the first fluid pathway 195 extending through the body 100 from an opening (i.e., opening 131 of FIG. 2) in the first reservoir 130 to an opening 121b in the processing chamber 120. Disposed in the first fluid pathway 195 (i.e., in the processing chamber 120 proximate the second end 114 of the body 100) is a filter 160. The filter has a first side 162 that is oriented in the first fluid pathway 195 toward the processing chamber 120. In the illustrated embodiment, the filter 160 is secured in its operable position by a retaining structure 168 (e.g., an O-ring that is secured in place via friction fit or by an adhesive, for example). The filter 160 is not shown in FIG. 2 in order to show the openings (121a, 121b, 131, and 141, respectively) and the one-way valves (172 and 174, respectively).

The at least one wall (e.g., wall 132) of the first reservoir 130 and first one-way valve 172 (discussed below) define a second operational volume (e.g., the inner volume of the first reservoir). The second operational volume can be selected from a variety of volumes that are suitable for processing samples. In any embodiment, the first reservoir 130 contains a liquid (not shown in FIG. 1) that is used to dilute, wash, and/or resuspend (e.g., concentrate) sample material that is processed in the processing chamber 120. Accordingly, the second operational volume may be selected based on a number of factors of the method in which the apparatus is used. A person having ordinary skill in the art will recognize these factors include, for example, how many times a sample material is washed, the volume of liquid used for each wash step, the final volume in which a sample material is diluted or resuspended. In any embodiment, the second operational volume is less than the first operational volume. In any embodiment, the second operational volume is approximately equal to the first operational volume. In any embodiment, the second operational volume is greater than the first operational volume.

In any embodiment, the first reservoir 130 optionally may comprise a back-flush liquid 136. The back-flush liquid is urged from the first reservoir 130 through the filter 160 as described below. As it is urged through the filter 160, the back-flush liquid 136 may wash and, optionally, resuspend particulate material (e.g., particulate material such as microorganisms) deposited on the filter. In any embodiment, the back-flush liquid 136 may comprise water. In any embodiment, the back-flush liquid 136 may comprise a surfactant. In any embodiment, the back-flush liquid 136 may comprise one or more solute (e.g., a salt, a sugar) to maintain a predetermined ionic strength or osmotic strength.

In any embodiment, the filter 160 may be configured to substantially prevent the passage of biological cells from the processing chamber 120 to the second reservoir 140. In any embodiment, this can be accomplished by using a filter 160 that has a nominal pore size that is smaller than a typical biological cell. Membrane filters are non-limiting examples of materials that are suitable for use as the filter 160 in any embodiment of the apparatus of the present disclosure. Membrane filters having a nominal porosity of 0.45 µm or 0.2 µm, for example, are suitable to retain microbial cells. Membrane filters having a nominal porosity of 0.45 µm or 0.2 µm, for example, are suitable to retain microbial cells. Membrane filters having a nominal porosity up to about 10 µm, for example, are suitable to retain yeast cells, mold cells, plant cells or animal cells.

In any embodiment, the filter 160 may be configured (e.g., by its location, size, shape, and nominal pore size) to substantially prevent the passage of cell concentration agents (e.g., particles such as antibody-conjugated particles that are adapted to bind biological cells) from the processing chamber to the first reservoir 130 and/or to the second reservoir 140. Nonlimiting examples of suitable cell concentration agents include activated charcoal, hydroxyapatite (Berry et al.; Appl. Environ. Microbiol.; 63:4069-4074; 1997), magnetic beads (Oster et al., J. Magnetism and Magnetic Mat.; 225:145-150; 2001), ferrimagnetic mineral, magnetite, chitosan, and affinity supports. Other examples of suitable concentration agents can be found in U.S. Patent Application Publication No. 2010/0062421; the disclosure of which is incorporated herein by reference in its entirety.

When the filter 160 is configured to substantially prevent the passage of cell concentration agents, the nominal pore size of the filter may be larger than the cells that are bound to the cell concentration agents. By preventing the passage of the cell concentration agents, the filter 160 can keep the cell concentration agents and any biological cells adhered thereto accessible for processing in the processing chamber 120, as described herein. In these embodiments, a suitable pore size for the filter 160 can be about 1 micron, about 2 microns, about 5 microns or greater. In these embodiments, a person having ordinary skill in the art will recognize the pore size of the filter can be selected according to the size (e.g., median diameter) of the cell concentration agent.

Advantageously, in these embodiments, the use of a filter having a larger pore size may enable more-rapid filtration rates.

A first one-way valve 172 is disposed in the first fluid pathway 195 between the filter 160 and the first reservoir 130. The first one-way valve 172 provides selective (e.g., directionally-selective, operationally selective) fluid communication between the processing chamber 120 and the first reservoir 130. Suitable one-way valves for use as the first one-way valve 172 include, for example, Bellville-type, umbrella-type, and duck-bill type one-way valves. Operational selectivity can be maintained by using a one-way valve that has a defined cracking pressure (i.e., a threshold positive or negative pressure that causes the valve to open) that must be exceeded in order to permit the passage of fluid through the first one-way valve 172. Thus, in any embodiment, the first one-way valve 172 comprises a pressure-actuated one-way valve. Directional selectivity can be maintained by aligning the first one-way valve 172 in the first fluid pathway 195 so that it facilitates substantially unidirectional fluid flow. In any embodiment, the first one-way valve 172 facilitates substantially unidirectional liquid flow from the first reservoir 130 to the processing chamber 120. Accordingly, the first one-way valve 172 substantially prevents liquid flow from the processing chamber 120 to the first reservoir 130.

The second reservoir 140 is also in fluid communication with the processing chamber 120. FIG. 3a shows a detail view of the second fluid pathway 197 extending from the second reservoir 140 through the filter 160 and into the processing chamber 120. The second fluid pathway 197 passes through the opening 141 in the second reservoir 140, the opening 121a in the processing chamber 120 and the filter (filter 160 of FIGS. 3 and 3a, not shown in FIG. 2). Thus, both the first fluid pathway 195 and second fluid pathway 197 pass through the filter.

A second one-way valve 174 is disposed in the second fluid pathway 197 between the filter 160 and the second reservoir 140. The second one-way valve 174 provides selective (e.g., directionally-selective, operationally selective) fluid communication between the processing chamber 120 and the second reservoir 140. Suitable one-way valves for use as the second one-way valve 174 include, for example, Bellville-type, umbrella-type, and duck-bill type one-way valves. Operational selectivity can be maintained by using a one-way valve that has a defined cracking pressure (i.e., a threshold positive or negative pressure that causes the valve to open) that must be exceeded in order to permit the passage of fluid through the second one-way valve 174. Thus, in any embodiment, the second one-way valve 174 comprises a pressure-actuated one-way valve. Directional selectivity can be maintained by aligning the second one-way valve 174 in the second fluid pathway 197 so that it facilitates substantially unidirectional fluid flow. In any embodiment, the second one-way valve 174 facilitates substantially unidirectional liquid flow from the processing chamber 120 to the second reservoir 140. Accordingly, the second one-way valve 174 substantially prevents liquid flow from the second reservoir 140 to the processing chamber 120.

The at least one wall (e.g., wall 142) of the second reservoir 140 and the second one-way valve 174 define a third operational volume (e.g., the inner volume of the second reservoir). The third operational volume can be selected from a variety of volumes that are suitable for processing samples. In any embodiment, the second reservoir 140 receives a portion (e.g., a filtrate, not shown in FIG. 1) of the liquid that comprised the sample to be processed. In addition, the second reservoir 140 optionally receives a portion of a liquid that is used to dilute and/or wash the sample material that is processed in the processing chamber 120. Accordingly, the third operational volume may be selected based on a number of factors of the method in which the apparatus is used. A person having ordinary skill in the art will recognize these factors include, for example, how many times a sample material is washed and the volume of liquid used for each wash step. In any embodiment, the third operational volume is less than the first operational volume. In any embodiment, the third operational volume is approximately equal to the first operational volume. In any embodiment, the third operational volume is greater than the first operational volume.

The first reservoir 130 and second reservoir 140 comprise openings (openings 134 and 144, respectively) proximate the first end 112 of the body 100. The openings 134 and 144 serve as vents to allow equilibration of pressure within each reservoir as liquid is transferred into or out of the reservoir. In any embodiment, it is contemplated that the vent (e.g., opening 134) in the first reservoir 130 and/or the vent (e.g., opening 144) in the second reservoir 140 may be substantially smaller than illustrated in FIGS. 1-3. In any embodiment, one or more of the vents (openings 134 or 144, respectively) may comprise a porous layer (e.g., a filter material, not shown) that substantially permits the passage of air into or out of the reservoir while substantially preventing the passage of biological cells into or out of the reservoir.

In any embodiment, an apparatus of the present disclosure may further comprise a water-absorbent material (not shown) disposed in the second reservoir. This material functions to absorb liquid transferred from the process chamber into the second reservoir. This reduces the possibility of significant leakage of liquid from the second reservoir if the apparatus is accidently tipped, tilted, dropped or cracked. Non-limiting examples of suitable water-absorbent materials include cellulosic fiber materials, starch-acrylonitrile copolymers, polyacrylate/polyacrylamide copolymers, and the like. In any embodiment, the absorbent material can be molded.

In another aspect, the present disclosure provides a method of processing a sample. According to the method, the sample can be processed in order to detect an indication of a microorganism that is present in the sample prior to processing the sample. Advantageously, the method can result in improved results such as faster and/or more-sensitive and/or more specific detection of the microorganism, for example. Without being bound by theory, these results can be facilitated by the method via 1) diluting the sample into a larger volume of liquid in order to lower a concentration of a substance that inhibits detection of the microorganism, 2) concentrating one or more biomolecules from the microorganism to be detected into a smaller volume of liquid, 3) filtering out of the sample a soluble substance that inhibits detection of the microorganism, and/or 4) performing concentration and cell lysis steps in a single container and thereby avoiding potential loss of material that may otherwise occur when transferring portions of a sample between separate containers that are used to perform those respective processes.

A method of processing a sample according to the present disclosure comprises placing a sample comprising a liquid into the processing chamber of any one of the embodiments of the apparatus for processing a sample disclosed herein. The method further comprises urging at least a portion of the liquid out of the processing chamber through the filter (e.g., into the second reservoir); after urging the at least a portion of the liquid through the filter, urging a first portion of a back-flush liquid from the first reservoir through the filter and into the process chamber to form a first processed sample; and analyzing at least a portion of the sample to detect an indication of a microorganism, wherein analyzing at least a portion of the sample comprises analyzing at least a portion of the first processed sample.

FIGS. 4a-4g show a series of cross-sectional views of an apparatus 1000 of the present disclosure during its use in one embodiment of a method of processing a sample according to the present disclosure.

FIG. 4a shows a sample 80 being placed (e.g., by pipetting, by pouring) into a processing chamber 120 of an apparatus 1000 of the present disclosure. The sample 80 comprises a liquid to facilitate processing according the present disclosure. The apparatus 1000 comprises a body 100 and a plunger 200. The body 100 has a first end 112 and a second end 114 opposite the first end. The body 100 comprises the processing chamber 120 comprising an opening 124 proximate the first end 112 of the body 100, a first reservoir 130 in selective fluid communication with the processing chamber via a first fluid pathway (not shown), a second reservoir 140 in selective fluid communication with the processing chamber via a second fluid pathway (not shown), and a filter 160 through which the first fluid pathway and the second fluid pathway pass. The processing chamber 120 is configured to receive the plunger 200, as described hereinabove.

Figure 7:
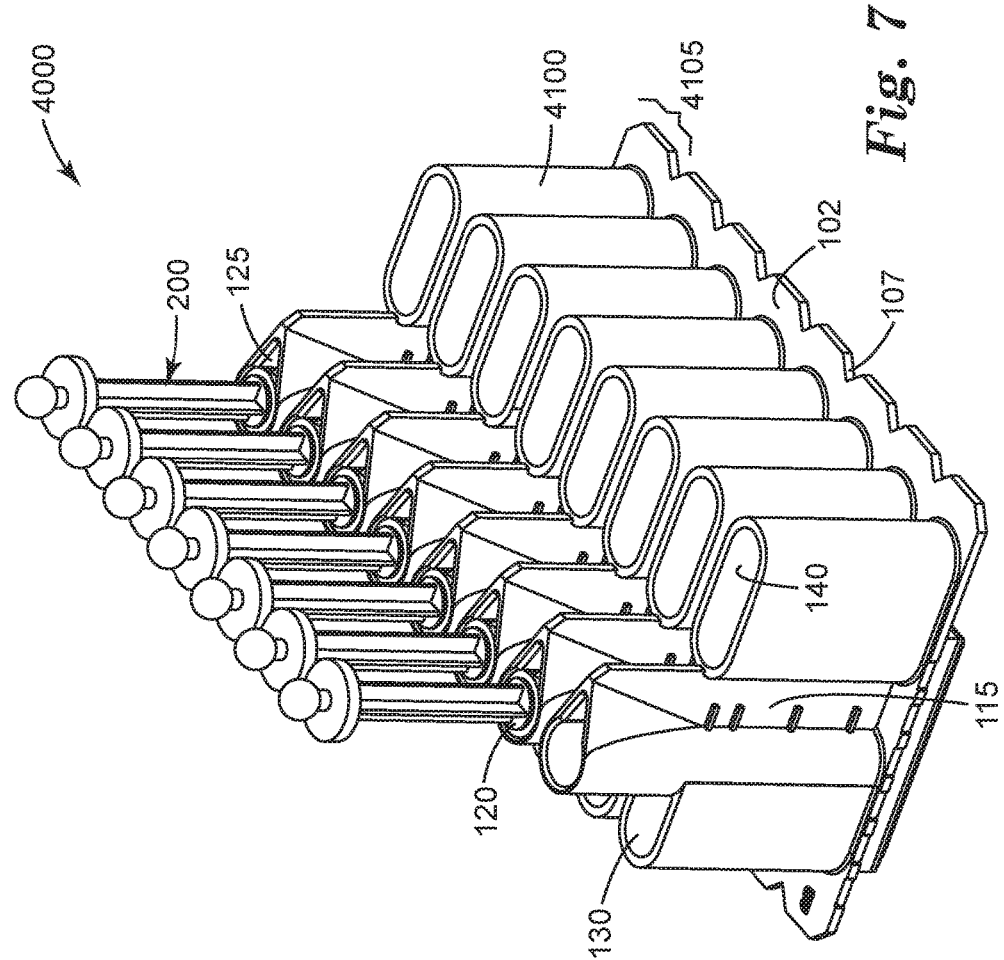
FIG. 7 is a top perspective view of another alternative embodiment of an apparatus for processing a plurality of samples, the apparatus comprising a plurality of sample-processing modules, each sample-processing module comprising a port.
Figure 8:
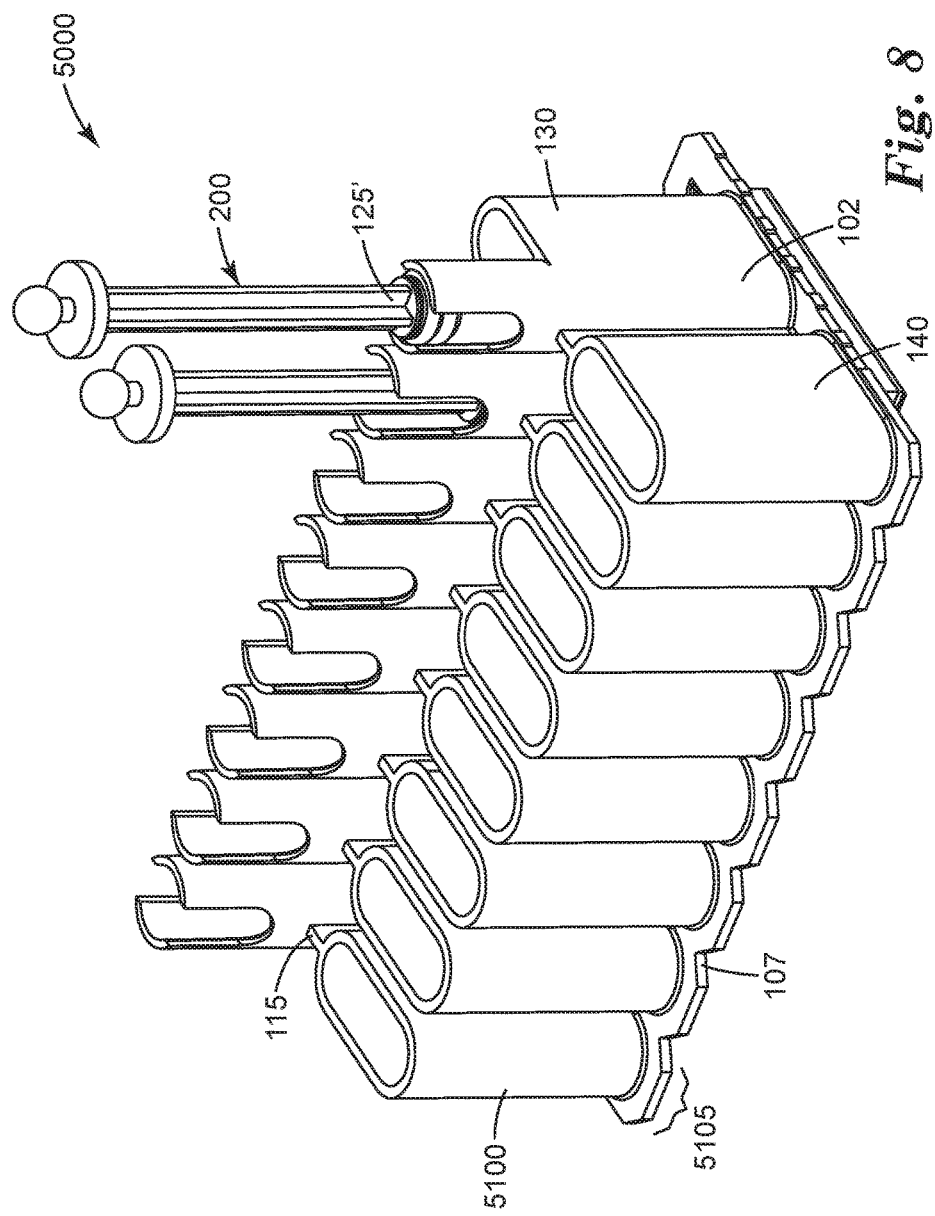
FIG. 8 is a top perspective view of yet another alternative embodiment of an apparatus for processing a plurality of samples, the apparatus comprising a plurality of sample-processing modules, each sample-processing module comprising a port.

In any embodiment, the sample 80 may be placed into the processing chamber 120 via a sample port (e.g., sample port 125 shown in FIG. 7 or sample port 125' shown in FIG. 8). In those embodiments, the plunger 200 may be partially inserted into the processing chamber 120 (as shown in FIG. 8) while the sample 80 is being placed into the chamber. Otherwise, after the sample 80 is deposited into the processing chamber 120, the plunger 200 is inserted into the processing chamber as shown in FIG. 4b.

In any embodiment, the amount of sample 80 placed in the processing chamber 120 may be a predetermined volume. In any embodiment, a first visual indicium (shown in FIG. 1) may be used by the operator in order to place a predetermined volume of the sample 80 into the processing chamber 120.

The method further comprises urging at least a portion of the liquid of the sample 80 through the filter 160. This can be accomplished by urging the plunger 200 through the processing chamber 120 toward the second end 114 of the body 100, as shown by arrow "A" in FIG. 4c. Urging the plunger 200 toward the second end 114 creates positive pressure in the processing chamber 120 which can open the second one-way valve 174, thereby permitting the liquid (i.e., the sample filtrate 190) to flow through the second fluid pathway 197 from the processing chamber through the second one-way valve 174 in into the second reservoir 140.

A person having ordinary skill in the art will recognize that, in an alternative embodiment (not shown), the fluid can be urged to flow through the filter 160 and into the second reservoir 140 by applying a negative pressure (e.g., using a vacuum pump) to the second reservoir 140. This embodiment does not require the use of a plunger 200 to move the liquid to the second reservoir 140.

After urging the at least a portion of the liquid through the filter 160, a first portion of the back-flush liquid 136 is urged via the first fluid pathway 195 from the first reservoir 130 through the filter 160 and into the processing chamber 120, as shown in FIG. 4d. In order to urge a first portion of the back-flush liquid 136 from the first reservoir 130 through the filter 160, the plunger 200 can be moved (e.g., withdrawn) through the processing chamber 120 toward the first end 112 of the body 100, as shown in FIG. 4d. Withdrawing the plunger 200 toward the first end 112 creates negative pressure in the processing chamber 120 which can open the first one-way valve 172, thereby permitting the liquid to flow through the first fluid pathway 195 from the first reservoir 130 through the first one-way valve 172 and into the processing chamber 120 to form a first processed sample 82. The first processed sample 82 comprises any particulate material 81 from the sample 80 that was retained by the filter 160, any liquid material from the sample 80 that was not urged through the filter 160, and any back-flush liquid 136 that was moved from the first reservoir 130 to the processing chamber 120.

A person having ordinary skill in the art will recognize alternative ways to urge a liquid to flow from the first reservoir 130 through the first fluid pathway 195 into the processing chamber 120. For example, in any embodiment, a negative pressure can be applied to the processing chamber 120 via an external vacuum source (e.g., a vacuum pump, not shown). Alternatively, a positive pressure may be applied to the first reservoir 130 (e.g., via a compressed gas or air, not shown, being applied to the first reservoir through a first reservoir vent, not shown).

In any embodiment of the method, the sample 80 has a first predetermined volume. In any embodiment, the first processed sample 82 has a second predetermined volume. In any embodiment, the second predetermined volume is greater than or equal to the first predetermined volume. In any embodiment, the second predetermined volume is less than or equal to the first predetermined volume. In any embodiment, the volume of the second predetermined volume is a predetermined fraction (e.g., ½, ⅓, ¼, ⅕, 1/10, 1/100) of the first predetermined volume. Thus, forming the first processed sample 82 may comprise concentrating the particulate material 81 of the sample 80 into a smaller volume. In any embodiment, forming the first processed sample 82 may comprise using a visual indicium (not shown) on the processing chamber or the first reservoir to produce a first processed sample 82 having the second predetermined volume. For example, a visual indicium denoting a volume in the processing chamber 120 may be used to determine that a proper volume of back-flush liquid 136 is transferred through the filter 160 and into the processing chamber. Alternatively, a visual indicium denoting a volume in the first reservoir 130 may be used to determine that a proper volume of back-flush liquid 136 is transferred through the filter 160 and into the processing chamber 120.

After the first processed sample 82 is formed, a portion of the first processed sample can be analyzed to detect an indication of a microorganism. The portion can be analyzed using a variety of analytical methods known in the art. Optionally, before analyzing a portion of the first processed sample 82, the temperature of the processing chamber 120 (with the first processed sample 82 therein) can be adjusted to about 95-100° C. in order to make cells permeable so that intracellular molecules (e.g., nucleic acids) can be detected. Alternatively, the portion of first processed sample 82 can be removed from the processing chamber 120 (e.g., by pipette) and transferred into a reaction tube before heat-treating the portion. In any embodiment, the temperature can be adjusted, for example, by placing the apparatus 1000 into a heated device (e.g., an incubator or a water bath, not shown). Advantageously, the entire compact apparatus 1000 can be placed into the heated device in order to adjust the temperature of the processing chamber 120.

Alternatively, and/or in addition to analyzing a portion of the first processed sample 82, at least a portion of the first processed sample is urged out of the processing chamber 120 through the filter 160 and into the second reservoir 140 as illustrated in FIG. 4e. The portion can be urged through the filter 160. This can be accomplished by urging the plunger 200 through the processing chamber 120 toward the second end 114 of the body 100, as shown by arrow "A" as described above. Urging the plunger 200 toward the second end 114 creates positive pressure in the processing chamber 120 which can open the second one-way valve 174, thereby permitting the liquid to flow through the second fluid pathway 197 from the processing chamber through the second one-way valve 174 in into the second reservoir 140 where it mixes with the sample filtrate 190 to form the diluted sample filtrate 191.

After urging the at least a portion of the liquid of the first processed sample 82 through the filter 160, a second portion of the back-flush liquid 136 is urged via the first fluid pathway 195 from the first reservoir 130 through the filter 160 and into the processing chamber 120, as shown in FIG. 4f. In order to urge a second portion of the back-flush liquid 136 from the first reservoir 130 through the filter 160, the plunger 200 can be moved (e.g., withdrawn) through the processing chamber 120 toward the first end 112 of the body 100, as shown in FIG. 4f. Withdrawing the plunger 200 toward the first end 112 creates negative pressure in the processing chamber 120 which can open the first one-way valve 172, thereby permitting the liquid to flow through the first fluid pathway 195 from the first reservoir 130 through the first one-way valve 172 and into the processing chamber 120 to form a second processed sample 84. The second processed sample 84 comprises any particulate material 81 from the sample 80 that was retained by the filter 160, any liquid material from the sample 80 that was not urged through the filter 160, and any back-flush liquid 136 that was moved from the first reservoir 130 to the processing chamber 120.

In any embodiment of the method, the sample 80 has a first predetermined volume. In any embodiment, the second processed sample 84 has a third predetermined volume. In any embodiment, the third predetermined volume is greater than or equal to the first predetermined volume. In any embodiment, the third predetermined volume is less than or equal to the first predetermined volume. In any embodiment, the volume of the third predetermined volume is a predetermined fraction (e.g., ½, ⅓, ¼, ⅕, ⅒, ¹⁄₁₀₀) of the first predetermined volume. Thus, forming the second processed sample 84 may comprise concentrating the particulate material 81 of the sample 80 into a smaller volume. In any embodiment, forming the second processed sample 84 may comprise using a visual indicium (not shown) on the processing chamber or the first reservoir to produce a second processed sample 84 having the third predetermined volume. For example, a visual indicium denoting a volume in the processing chamber 120 may be used to determine that a proper volume of back-flush liquid 136 is transferred through the filter 160 and into the processing chamber. Alternatively, a visual indicium denoting a volume in the first reservoir 130 may be used to determine that a proper volume of back-flush liquid 136 is transferred through the filter 160 and into the processing chamber 120.

After the second processed sample 84 is formed, a portion of the second processed sample can be analyzed to detect an indication of a microorganism. The portion can be analyzed using a variety of analytical methods known in the art. Optionally, before analyzing a portion of the second processed sample 84, the temperature of the processing chamber 120 (with the second processed sample 84 therein) can be adjusted to about 95-100° C. in order to make cells permeable so that intracellular molecules (e.g., nucleic acids) can be detected. In any embodiment, the temperature can be adjusted, for example, by placing the apparatus 1000 into a heated device (e.g., an incubator or a water bath, not shown). Advantageously, the entire compact apparatus 1000 can be placed into the heated device in order to adjust the temperature of the processing chamber 120. Preferably, the plunger is removed from the process chamber before the apparatus is heated, thereby preventing a build-up of pressure in the processing chamber during heating.

After forming the first processed sample 82 or second processed sample 84, a portion of either (or both) processed sample(s) is analyzed to detect an indication of a microorganism. Optionally, the processed sample may be heat-treated before it is analyzed to detect an indication of a microorganism. The heat treatment may be conducted in the apparatus 1000 as described herein, or portions of the processed sample(s) may be removed from the apparatus for heat treatment. The second processed sample 84, or a portion thereof, can be removed from the processing chamber 120 before or after heat treatment by removing the plunger 200 from the processing chamber, as shown in FIG. 4h, and withdrawing the second processed sample with a pipette.

Analyzing at least a portion of the first processed sample or analyzing at least a portion of the second processed sample to detect an indication of a microorganism can be performed using a variety of processes known in the art. In any embodiment, analyzing at least a portion of the first processed sample or second processed sample comprises detecting an indication of a microorganism using a microorganism culture technique (e.g., growth on semi-solid culture medium, growth in liquid culture medium) to detect a viable microorganism. In any embodiment, analyzing at least a portion of the first processed sample or second processed sample comprises detecting an indication of a microorganism using biochemical detection techniques (e.g., detecting an antigen, a nucleic acid, an enzyme activity or a unique set of metabolites i.e. in an e-nose sensor). In any embodiment, analyzing at least a portion of the first processed sample or second processed sample comprises a combination of a culture technique and a biochemical detection technique.

In any embodiment, analyzing at least a portion of the first processed sample or second processed sample comprises detecting an indication of a microorganism using a nucleic acid detection technique. In a preferred embodiment, the portion is analyzed using a Molecular Detection System available from 3M Company (St. Paul, Minn.).

In yet another aspect, the present disclosure provides an apparatus for processing a plurality of samples. The apparatus comprises a plurality of sample-processing modules. In any embodiment, a plurality of modules in the apparatus can be used to process different samples. In any embodiment, a plurality of modules in the apparatus can be used to process different portions (e.g., replicate portions) of the same sample.

Figure 5:
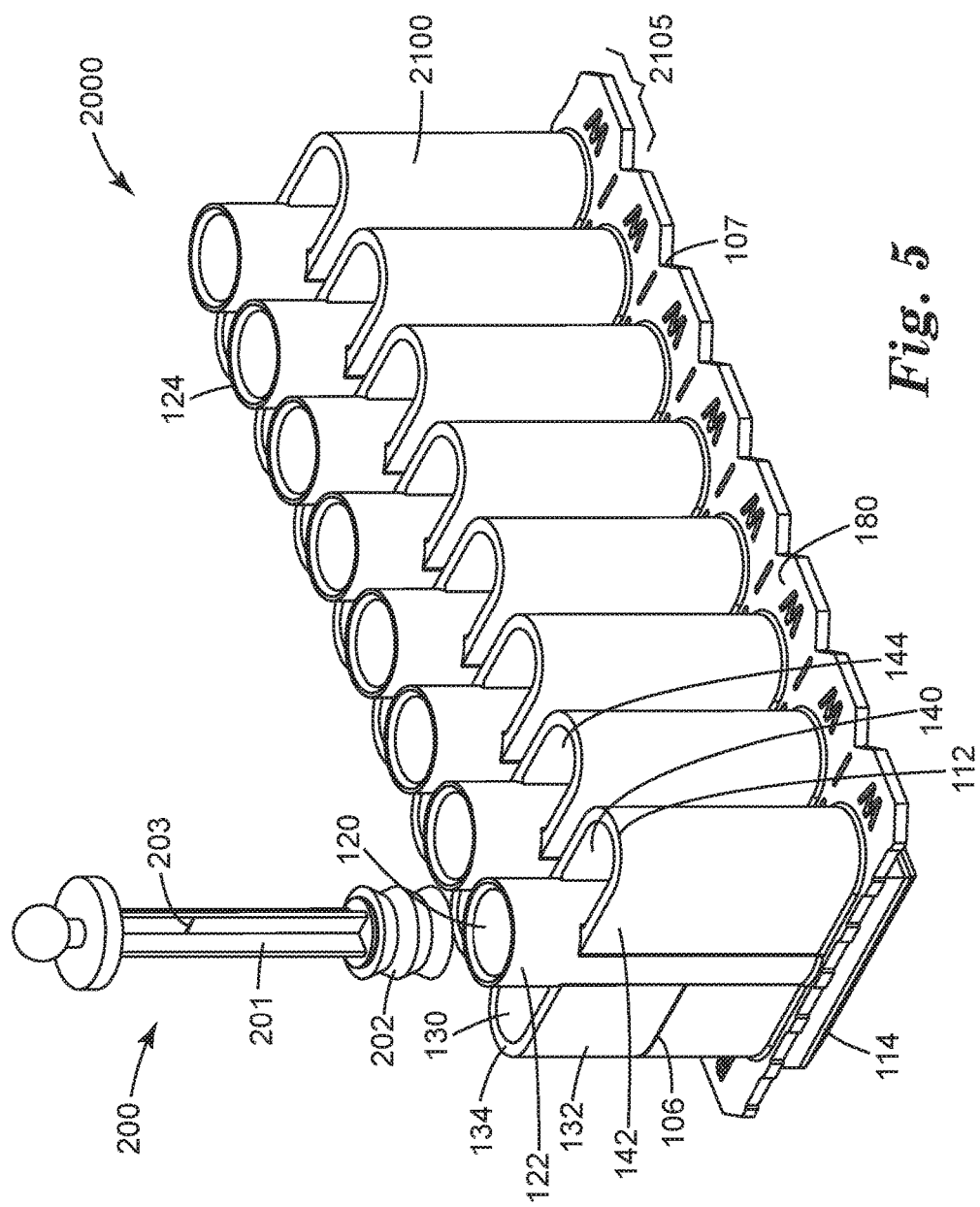
FIG. 5 is a partially-exploded, top perspective view of one embodiment of an apparatus for processing a plurality of samples, the apparatus comprising a plurality of sample-processing modules according to the present disclosure.

Turning back to the drawings, FIG. 5 shows one embodiment of an apparatus 2000 for processing a plurality of samples. The apparatus 2000 comprises a body 2100. The body 2100 comprises a plurality of sample-processing modules 2105. Thus, the body 2100 comprises at least a first sample-processing module and a second sample-processing module, the first module in the body being coupled to the second module in the body. The sample-processing modules 2105 can be detachably coupled to each other, as described below.

Optionally, the apparatus 2000 comprises at least one plunger 200. In any embodiment, the apparatus may comprise a plurality of plungers (not shown). In any embodiment (not shown), the plurality of plungers may be operatively coupled, spaced-apart, and aligned so that each plunger can be inserted into a separate sample-processing module but the plurality of plungers can be moved as a unit.

Returning to FIG. 5, the body 2100 comprises a first end 112 and a second end 114 opposite the first end. The body 2100 further comprises eight sample-processing modules 2105. Each sample-processing module 2105 comprises a processing chamber 120, a first reservoir 130, and a second reservoir 140; each processing chamber, first reservoir and second reservoir as described above. The optional plunger 200 comprises a stem portion 201 and sealing member 202, as described above.

The body 2100 and at least a portion (e.g., the stem portion 201) of the plunger 200 can be fabricated using materials and processes that are known in the art. For example, the body 2100 and plunger 200 may be made by conventional molding processes using a suitable polymeric material (e.g., polyethylene, polypropylene, polystyrene, polycarbonate, Acrylonitrile Butadiene Styrene (ABS) plastic). In any embodiment, the material from which the body 2100 is made is optically transmissible (i.e., the material is transparent or translucent. Advantageously, this permits the operator using the apparatus 2000 to observe, for example, the status of the plunger 200 or a liquid level (e.g., a sample liquid, a liquid in the first reservoir 130 and/or second reservoir 140) as the apparatus 2000 is being used.

Optionally, in any embodiment, the sealing member 202 can be made from a more-conformable material (e.g., butyl rubber, silicone rubber, oil-impregnated silicone rubber) using conventional processes (e.g., molding processes) that are known in the art. In these embodiments, the sealing member 202 is coupled to the stem portion 201 using any one of a variety of means (e.g., press-fit, adhesive means such as a pressure-sensitive adhesive, an ultrasonic weld).

The processing chamber 120 of each sample-processing module 2105 has an opening 124 proximate the first end 112 of the body 2100. The opening 124 is configured (e.g., shaped and dimensioned) to receive at least a portion of the plunger 200.

The processing chamber 120 and first reservoir 130 of each sample-processing module 2105 are in selective fluid communication via a first fluidic pathway as described above and shown in FIG. 3a. Disposed in the first fluidic pathway between the first reservoir 130 and the processing chamber 120 of each sample-processing module 2105 is a first one-way valve similar to first one-way valve 172 as described above and shown in FIG. 3a. In addition, the processing chamber 120 and second reservoir 140 of each sample-processing module 2105 are in selective fluid communication via a second fluidic pathway as described above and shown in FIG. 3a. Disposed in the second fluidic pathway between the second reservoir 140 and the processing chamber 120 of each sample-processing module 2105 is a second one-way valve similar to second one-way valve 174 as described above and shown in FIG. 3a.

Disposed in the first fluid pathway of each sample-processing module 2105 (e.g., disposed in the processing chamber 120 proximate the second end 114 of the body 100) is a filter (not shown) as described above and as shown in FIG. 3a, for example. The filter has a first side that is oriented in the first fluid pathway toward the processing chamber. The filter may be secured in its operable position by a retaining structure as described above.

The processing chamber 120, the first reservoir 130, and the second reservoir 140 comprise at least one wall that defines the shape and inner volume of the respective structure. A person having ordinary skill in the art in view of the present disclosure will recognize the processing chamber, the first reservoir, and the second reservoir can define a variety of shapes and sizes that are suitable for use as described herein. For example, the processing chamber 120 of the illustrated embodiment of FIG. 5 comprises a wall 122 that defines a cylindrically-shaped processing chamber. The first reservoir 130 is defined in part by walls 122 and 132, respectively. The second reservoir 140 is defined in part by walls 122 and 142, respectively. Thus, in any embodiment, the first reservoir 130 and/or the second reservoir 140 is immediately adjacent the processing chamber 120 in each respective sample-processing module 2105. Advantageously, this configuration (i.e., the reservoirs immediately adjacent the processing chamber) affords a substantially compact design. In addition, the sample-processing modules 2105 can be disposed in a linear array with substantially uniform spacing between the openings 124 of the processing chambers 120. Advantageously, this configuration may permit the operator to use a multichannel pipettor when processing a plurality of samples simultaneously.

The at least one wall (e.g., wall 122) of the processing chamber 120 and the filter (not shown) may define a first operational volume (e.g., the inner volume of the processing chamber) as discussed for the apparatus 1000 above. In any embodiment, the first operational volume of the processing chambers 120 of each plurality of sample-processing modules may be approximately equal. The first operational volume can be selected from a variety of volumes that are suitable for processing typical samples. In any embodiment, the first operational volume is at least about 0.02 mL to about 100 mL. In any embodiment, the first operational volume is at least about 0.02 mL to about 25 mL. In any embodiment, the first operational volume is at least about 0.02 mL to about 10 mL. In any embodiment, the first operational volume is about 1 mL to about 100 mL. In any embodiment, the first operational volume is 1 mL to about 5 mL.

In any embodiment, the body 100 of the apparatus 2000 further comprises one or more visual indicium 106 to indicate a predetermined volume, as discussed above. The one or more visual indicium can indicate a predetermined volume in the first reservoir 130 of any sample-processing module 2105 of the apparatus 2000. In alternative embodiments, not shown, the one or more visual indicium may indicate a predetermined volume in the processing chamber and/or the second reservoir of any sample-processing module.

The wall 122 of each processing chamber 120 and at least a portion (e.g., the stem portion 201 and the sealing member 202) of each plunger 200 are configured so that at least part of the plunger can be removably inserted into the processing chamber and can slideably traverse through at least a portion of the processing chamber. Preferably, a portion (e.g., the sealing member 202) of the plunger 200 forms a substantially fluid-tight fit when engaged with the wall 122 in the processing chamber 120, thereby facilitating the establishment of positive or negative pressure in the processing chamber when the plunger is inserted in the processing chamber and urged toward the second end 114 or first end 112 of the body 2100.

Within each sample-processing module 2105, the first reservoir 130 is in fluid communication with the processing chamber 120 via a first fluid pathway as shown for apparatus 1000 in FIG. 3a. Disposed in the first fluid pathway (i.e., in the processing chamber 120 proximate the second end 114 of the body 2100) is a filter (as shown in FIG. 3a). The filter has a first side that is oriented in the first fluid pathway toward the processing chamber 120 and is described in detail above. Optionally, the filter is secured in its operable position by a retaining structure, as discussed above.

The at least one wall (e.g., wall 132) of the first reservoir 130 and first one-way valve (discussed below) of each sample-processing module 2105 define a second operational volume (e.g., the inner volume of the first reservoir, as discussed above). The second operational volume can be selected from a variety of volumes that are suitable for processing samples. In any embodiment, the first reservoir 130 contains a liquid (not shown in FIG. 5) that is used to dilute, wash, and/or resuspend (e.g., concentrate) sample material that is processed in the processing chamber 120. Accordingly, the second operational volume may be selected based on a number of factors of the method in which the apparatus is used. A person having ordinary skill in the art will recognize these factors include, for example, how many times a sample material is washed, the volume of liquid used for each wash step, the final volume in which a sample material is diluted or resuspended. In any embodiment, the second operational volume is less than the first operational volume. In any embodiment, the second operational volume is approximately equal to the first operational volume. In any embodiment, the second operational volume is greater than the first operational volume.

In any embodiment, the first reservoir 130 of any sample-processing module 2105 optionally may comprise a back-flush liquid (not shown) similar to the back flush liquid 136 described above. The back-flush liquid is urged from the first reservoir 130 through the filter as described herein. As it is urged through the filter, the back-flush liquid may wash and, optionally, resuspend particulate material (e.g., particulate material such as microorganisms) deposited on the filter. In any embodiment, the back-flush liquid may comprise water. In any embodiment, the back-flush liquid may comprise a surfactant. In any embodiment, the back-flush liquid may comprise one or more solute (e.g., a salt, a sugar) to maintain a predetermined ionic strength or osmotic strength.

A first one-way valve (not shown) is disposed in the first fluid pathway of each sample-processing module 2105 between the filter and the first reservoir 130. The first one-way valve provides selective (e.g., directionally-selective, operationally selective) fluid communication between the processing chamber 120 and the first reservoir 130, as described for the apparatus 1000 above. Suitable one-way valves for use as the first one-way valve include duck-bill type one-way valves. Operational selectivity can be maintained by using a one-way valve that has a defined cracking pressure (i.e., a threshold positive or negative pressure that causes the valve to open) that must be exceeded in order to permit the passage of fluid through the first one-way valve. Thus, in any embodiment, the first one-way valve of any sample-processing module 2105 comprises a pressure-actuated one-way valve. Directional selectivity can be maintained by aligning the first one-way valve in the first fluid pathway so that it facilitates substantially unidirectional fluid flow. In any embodiment, the first one-way valve facilitates substantially unidirectional liquid flow from the first reservoir 130 to the processing chamber 120. Accordingly, the first one-way valve substantially prevents liquid flow from the processing chamber 120 to the first reservoir 130 in a sample-processing module 2105.

The second reservoir 140 is also in fluid communication with the processing chamber 120 in each sample-processing module 2105 via a second fluid pathway extending from the second reservoir through the filter and into the processing chamber, as shown in FIG. 3a and described above. Thus, both the first fluid pathway and second fluid pathway pass through the filter in each sample-processing module 2105.

A second one-way valve (not shown) is disposed in the second fluid pathway of each sample-processing module 2105 between the filter and the second reservoir, as shown in FIG. 3a and described above. The second one-way valve provides selective (e.g., directionally-selective, operationally selective) fluid communication between the processing chamber 120 and the second reservoir 140. Suitable one-way valves for use as the second one-way valve include duck-bill type one-way valves. Operational selectivity can be maintained by using a one-way valve that has a defined cracking pressure (i.e., a threshold positive or negative pressure that causes the valve to open) that must be exceeded in order to permit the passage of fluid through the second one-way valve. Thus, in any embodiment, the second one-way valve comprises a pressure-actuated one-way valve. Directional selectivity can be maintained by aligning the second one-way valve in the second fluid pathway so that it facilitates substantially unidirectional fluid flow. In any embodiment, the second one-way valve facilitates substantially unidirectional liquid flow from the processing chamber 120 to the second reservoir 140 in each sample-processing module 2105. Accordingly, the second one-way valve substantially prevents liquid flow from the second reservoir 140 to the processing chamber 120.

The at least one wall (e.g., wall 142) of the second reservoir 140 and the second one-way valve (not shown) of any sample-processing module 2105 define a third operational volume (e.g., the inner volume of the second reservoir). The third operational volume can be selected from a variety of volumes that are suitable for processing samples. In any embodiment, the second reservoir 140 receives a portion (e.g., a filtrate, not shown in FIG. 5) of the liquid that comprised the sample to be processed. In addition, the second reservoir 140 optionally receives a portion of a liquid that is used to dilute and/or wash the sample material that is processed in the processing chamber 120. Accordingly, the third operational volume may be selected based on a number of factors of the method in which the apparatus is used. A person having ordinary skill in the art will recognize these factors include, for example, how many times a sample material is washed and the volume of liquid used for each wash step. In any embodiment, the third operational volume is less than the first operational volume. In any embodiment, the third operational volume is approximately equal to the first operational volume. In any embodiment, the third operational volume is greater than the first operational volume.

The first reservoir 130 and second reservoir 140 comprise openings (openings 134 and 144, respectively) proximate the first end 112 of the body 100. The openings 134 and 144 serve as vents to allow equilibration of pressure within each reservoir of a sample-processing module 2105 as liquid is transferred into or out of the reservoir. In any embodiment, it is contemplated that the vent (e.g., opening 134) in the first reservoir 130 and/or the vent (e.g., opening 144) in the second reservoir 140 may be substantially smaller than illustrated in FIG. 5. In any embodiment, one or more of the vents (openings 134 or 144, respectively) may comprise a porous layer (e.g., a filter material, not shown) that substantially permits the passage of air into or out of the reservoir while substantially preventing the passage of biological cells into or out of the reservoir.

In any embodiment of the apparatus 2000, the body 2100 may further comprise one or more predetermined area of weakness 107 (e.g., perforations, a scored line, a notch) that facilitate detaching one or more sample-processing module 2105 from at least one other sample-processing module of the body 2100.

In any embodiment, an apparatus 2000 of the present disclosure may further comprise a water-absorbent material (not shown) disposed in the second reservoir of any of the sample-processing modules 2105. This material functions to absorb liquid transferred from the process chamber into the second reservoir. This reduces the possibility of significant leakage of liquid from the second reservoir if the apparatus is accidently tipped, tilted, dropped or cracked. Non-limiting examples of suitable water-absorbent materials include cellulosic fiber materials, starch-acrylonitrile copolymers, polyacrylate/polyacrylamide copolymers, and the like.

Figure 6:
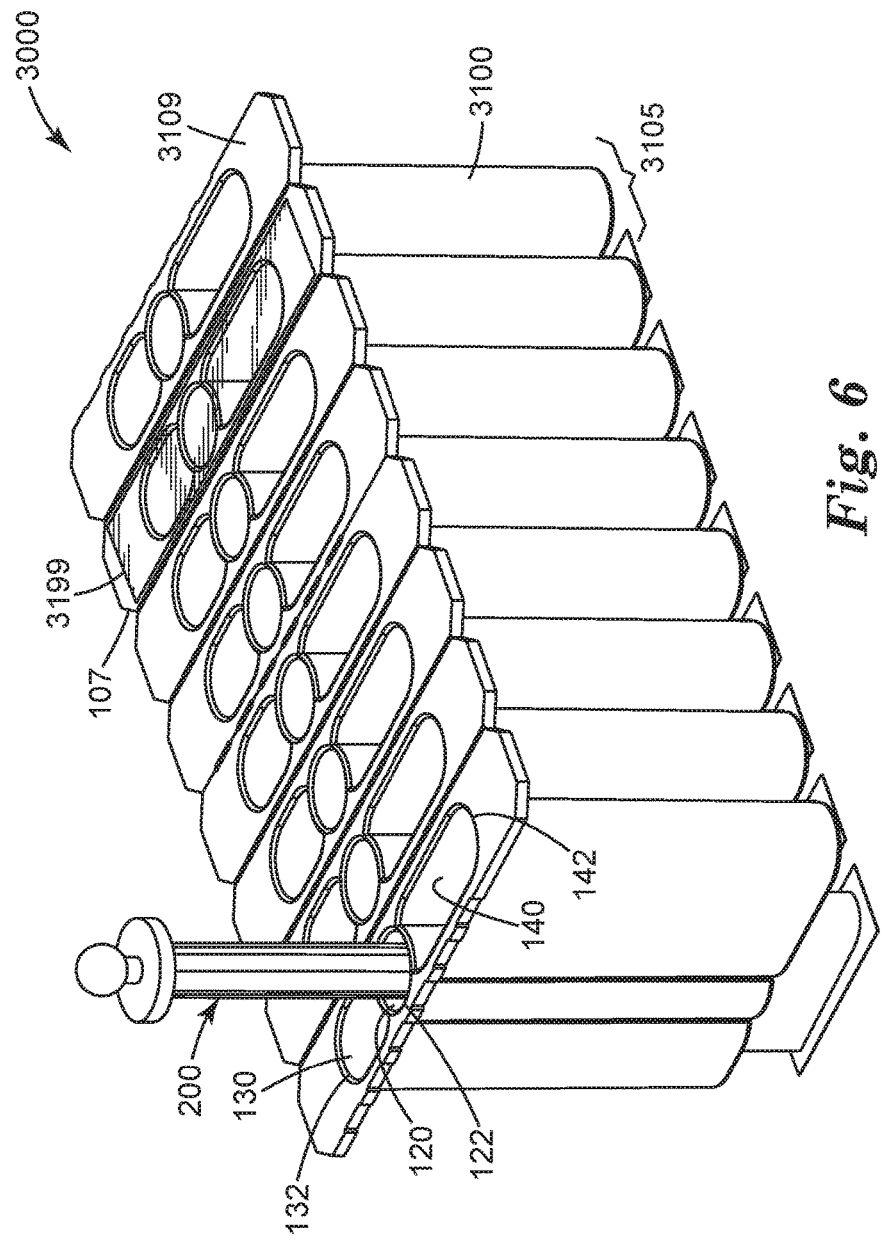
FIG. 6 is a top perspective view of an alternative embodiment of an apparatus for processing a plurality of samples, the apparatus comprising a plurality of sample-processing modules.

FIG. 6 shows a top perspective view of an alternative embodiment of an apparatus 3000 for processing a plurality of samples. The apparatus 3000 comprises a body 3100 comprising a plurality of sample-processing modules 3105. Each of the sample-processing modules 3105 comprises a processing chamber 120, first reservoir 130, second reservoir 140, and other components (e.g., first fluid pathway, second fluid pathway, first one-way valve, second one-way valve, and filter; none of which are shown in FIG. 6) that are described above with respect to apparatus 2000. In contrast to the apparatus 2000 of FIG. 5, the openings 124 of the processing chambers 120, the openings 134 of the first reservoirs 130, and the openings 144 of the second reservoirs 140 are substantially coplanar. In addition, the body 3100 comprises a flange 3109 that is substantially coplanar with the aforementioned openings. Advantageously, this configuration facilitates the application of a cover (e.g., cover 3199) to the body 3100 before and/or after use of the apparatus.

In any embodiment, the cover 3199 may be large enough to cover all of the openings (not shown). In any embodiment, the cover may comprise a film (e.g., a polyethylene or polypropylene film). In any embodiment, the cover 3199 may comprise an adhesive layer (e.g., a layer of pressure-sensitive adhesive, not shown). In any embodiment, the adhesive can be an adhesive that permits unsealing and resealing the cover 3199. The cover 3199 can substantially prevent contamination of any process chamber or reservoir before use, and may substantially reduce or prevent cross-contamination and/or leakage after use.

In any embodiment, the processing chamber 120 and reservoirs (first reservoir 130 and second reservoir 140) of each sample-processing module 3105 may comprise an individual cover 3199 as shown in FIG. 6. In these embodiments, the cover 3199 for one sample processing module 3105 may be removed as needed to process a sample while keeping the other individual covers in place to prevent accidental cross-contamination. In any embodiment, the cover 3199 may comprise a film such as, for example, a polyolefin sealing tape or an adhesive aluminum foil. In any embodiment, the cover 3199 may comprise a microporous film and, thus, may serve as a pressure vent during use. In any embodiment, the cover 3199 may be pierceable to permit addition or removal of materials from the reservoirs. In any embodiment (not shown), a single cover may be used to cover a plurality of reservoirs (e.g., either the first reservoirs or the second reservoirs). In any embodiment (not shown), a first cover may be used to cover a plurality (e.g., all) of the first reservoirs in a body and a second cover may be used to cover a plurality (all) of the second reservoirs.

Optionally, one or more of the first reservoirs and/or second reservoirs may comprise an actuatable drain (not shown). The drain may permit the operator to remove residual fluid from the first and/or second reservoirs after processing a sample.

In any embodiment of the apparatus 3000, the body 3100 may further comprise one or more predetermined areas of weakness 107 (e.g., perforations, a scored line, a notch) that facilitate detaching one or more sample-processing module 3105 from at least one other sample-processing module of the body 3100.

FIG. 7 shows a top perspective view of another alternative embodiment of an apparatus 4000 for processing a plurality of samples. The apparatus 4000 comprises a body 4100 comprising a plurality of sample-processing modules 4105. Each of the sample-processing modules 4105 comprises a processing chamber 120, first reservoir 130, second reservoir 140, and other components (e.g., first fluid pathway, second fluid pathway, first one-way valve, second one-way valve, and filter; none of which are shown in FIG. 7) that are described above with respect to apparatus 2000. In contrast to the apparatus 2000 of FIG. 5, the processing chambers 120 each comprise a port 125. The port 125 can be used, for example, to deposit a sample into a processing chamber 120 without completely removing the plunger 200 from the body 4100 of the apparatus 4000. In addition to the port 125, the body 4100 is configured so that each of the second reservoirs 140 is spaced-apart from the corresponding processing chamber 120 in each of the sample-processing modules 4105. In the illustrated embodiment of FIG. 7, the processing chambers 120 and second reservoirs 140 are spaced apart by a joining wall 115. Advantageously, this configuration (i.e., the process chambers being spaced apart from the second reservoirs) facilitates more-rapid heating of the contents of the processing chambers 120 when the apparatus 4000 is placed in a heating device. In the absence of the spaced-apart configuration, the second reservoir and any liquid therein could act as a heat sink in contact with the processing chamber, thereby acting to resist rapid temperature transitions in the processing chamber.

In any embodiment of the apparatus 4000, the body 4100 may further comprise one or more predetermined areas of weakness 107 (e.g., perforations, a scored line, a notch) that facilitate detaching one or more sample-processing module 4105 from at least one other sample-processing module of the body 4100. In any embodiment of the apparatus, the body further may comprise a base such as, for example, the base 102 shown in FIG. 7. In any embodiment, the base 102 may comprise the predetermined areas of weakness 107.

FIG. 8 shows a top perspective view of yet another alternative embodiment of an apparatus 5000 for processing a plurality of samples. The apparatus 5000 comprises a body 5100 comprising a plurality of sample-processing modules 5105. Each of the sample-processing modules 5105 comprises a processing chamber 120, first reservoir 130, second reservoir 140, and other components (e.g., first fluid pathway, second fluid pathway, first one-way valve, second one-way valve, and filter; none of which are shown in FIG. 7) that are described above with respect to apparatus 5000. The apparatus 5000 comprises an alternative embodiment of a port 125' that, similar to the port 125 of the apparatus 4000 described above, can be used, for example, to deposit a sample into a processing chamber 120 without completely removing the plunger 200 from the body 5100 of the apparatus 5000. Also similar to the apparatus 4000 described above, the body 5100 comprises a plurality of joining walls 115 that function to space apart each processing chambers 120 from each second reservoir 140 in each of the respective sample-processing modules 5105.

In any embodiment of the apparatus 5000, the body 5100 may further comprise one or more predetermined areas of weakness 107 (e.g., perforations, a scored line, a notch) that facilitate detaching one or more sample-processing module 5105 from at least one other sample-processing module of the body 5100.

Figure 9:
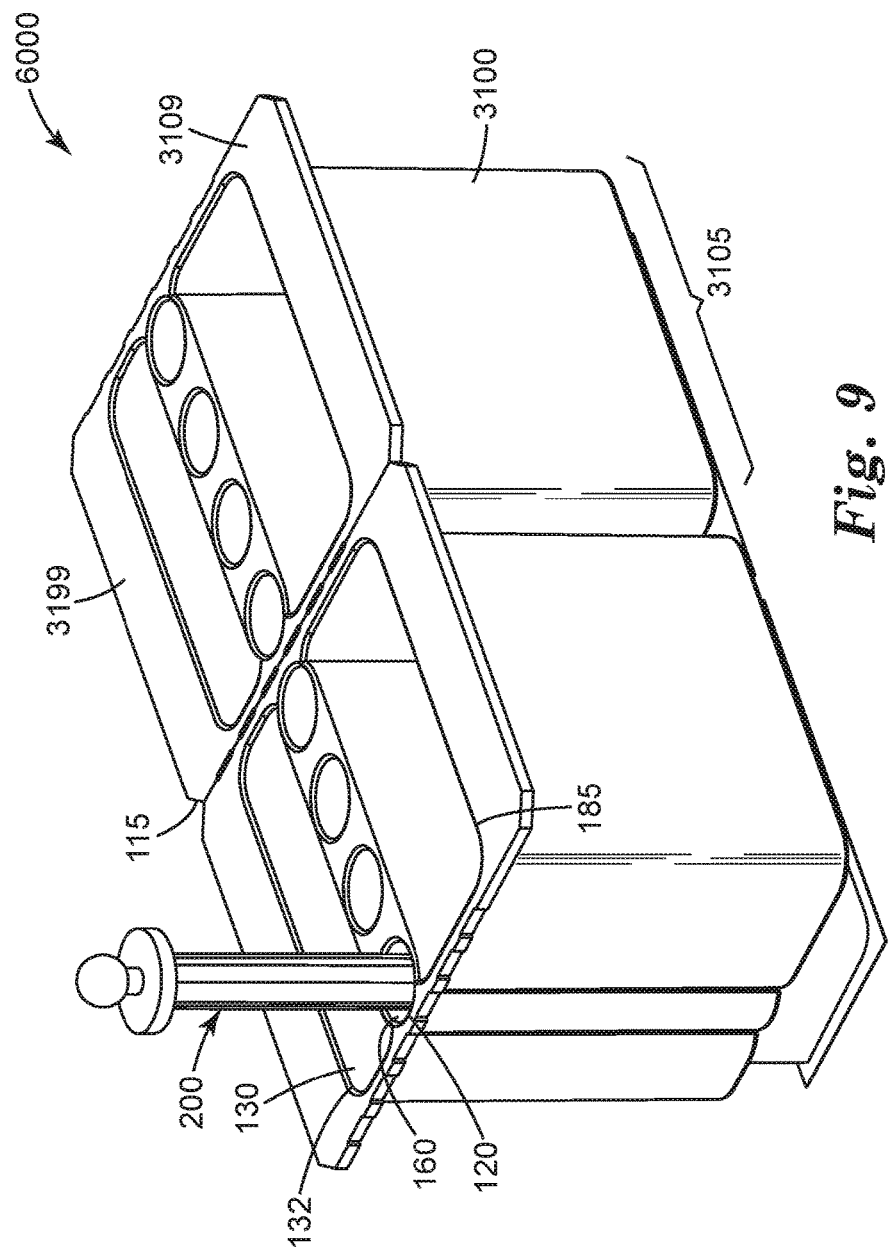
FIG. 9 is a top perspective view of one embodiment of an apparatus for processing a plurality of samples, the apparatus comprising a plurality of sample-processing modules that are in selective fluid communication with a mutual reservoir.
Figure 10:
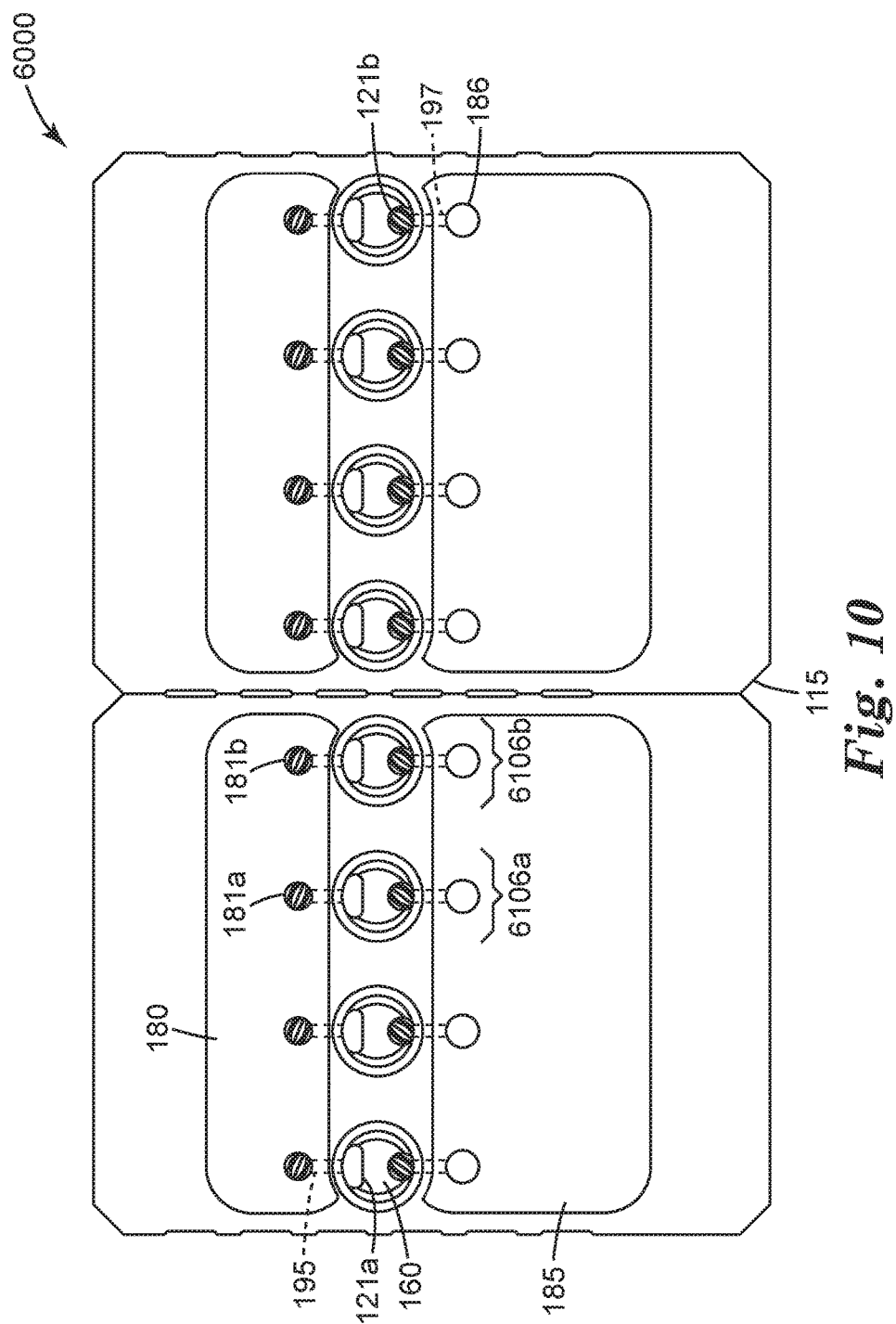
FIG. 10 is a top view of the apparatus of FIG. 9.

FIGS. 9 and 10 show various views of yet another alternative embodiment of an apparatus 6000 for processing a plurality of samples. The apparatus 6000 comprises a body 6100 comprising a plurality of sample-processing modules 6106. Each of the sample-processing modules 6106 comprises a processing chamber 120, first reservoir 180, second reservoir 185, first fluid pathway 195, second fluid pathway 197, filter 160, and other components (e.g. first one-way valve and second one-way valve, not shown in FIGS. 9 and 10) that are described above with respect to apparatus 2000, apparatus 3000, apparatus 4000, and apparatus 5000. The apparatus 6000 comprises a port 125' that, similar to the port 125 of the apparatus 4000 described above, can be used, for example, to deposit a sample into a processing chamber 120 without completely removing the plunger 200 from the body 6100 of the apparatus 6000. In contrast to other apparatuses for processing a plurality of samples described herein, the apparatus 6000 comprises a first reservoir 180 that is in selective fluid communication with a plurality of processing chambers 120 via a plurality of distinct first fluid pathways 195.

The illustrated embodiment shows that two sample-processing modules (first sample-processing module 6106a and second sample-processing module 6106b, respectively) if the apparatus 6000 each comprise separate processing chambers 120, filters 160, first fluid pathways 195, and second fluid pathways 197. However, openings 181a and 181b of the first sample-processing module 6106a and second sample-processing 6106b, respectively open into a common reservoir (i.e., first reservoir 180). Additionally as shown in FIG. 10, or alternatively, the openings 186 of both the first sample-processing module 6106a and second sample-processing 6106b, respectively, open into a second reservoir 185.

Although each of the first fluid pathways 195 in apparatus 6000 are shown as being operatively connected to a plurality of distinct openings 181 in the first reservoir 180, it is contemplated that, in an alternative embodiment, not shown, a plurality of first fluid pathways could be operatively connected to a mutual opening in the first reservoir.

Although each of the second fluid pathways 197 in apparatus 6000 are shown as being operatively connected to a plurality of distinct openings 186 in the second reservoir 185, it is contemplated that, in an alternative embodiment, not shown, a plurality of second fluid pathways could be operatively connected to a mutual opening in the second reservoir.

In any embodiment, the body 6100 may further comprise predetermined areas of weakness 107 (e.g., perforations, scored lines) that facilitate detaching one or more sample-processing module from at least one other sample-processing module of the body 6100.

Any embodiment of the method of processing a sample disclosed herein can be performed using any embodiment of the apparatus for processing a plurality of samples disclosed herein. Advantageously, using an apparatus for processing a plurality of samples, the plurality of samples can be processed sequentially (e.g., in separate sample-processing modules in a sequential order) or the plurality of samples may be processed simultaneously (i.e., in separate sample-processing modules at the same time).

In any embodiment, a plunger 200 used in an apparatus of the present disclosure further can comprise at least one plunger indicium 203. The plunger indicium 203, when inserted into the processing chamber 120 so that the plunger indicium 203 is approximately aligned with the opening 124 of the processing chamber, can indicate a predetermined volume of liquid has been expelled from the processing chamber. Alternatively, when the plunger 200 is fully inserted into the processing chamber 120 and then withdrawn until the plunger indicium 203 is approximately aligned with the opening 124 of the process chamber, this can indicate a predetermined volume of a liquid (not shown in FIG. 5) has been transferred from the first reservoir 130 to the processing chamber. In any embodiment of a method according to the present disclosure, a plunger indicium 203 can be used in conjunction with a first visible indicium or second visible indicium on the body of the apparatus (see visible first indicium 106 and second visible indicium 108, respectively of FIG. 1) in order to move predetermined volumes of liquid into or out of the processing chamber 120 while conducting the method.

In another aspect, the present disclosure provides a kit. The kit can comprise any embodiment of the apparatuses disclosed herein. In any embodiment, the kit further comprises a reagent. Suitable reagents include, for example, a sample resuspension liquid, a cell lysis reagent, a reagent used in a nucleic acid amplification reaction, and a reagent used in an antigen detection reaction.

A sample-resuspension liquid can be any liquid suitable for resuspending particulate materials retained by the filter of the apparatus and/or any liquid suitable for diluting any components (e.g., liquids, dissolved solutes, particulate materials) present in the original sample material. In any embodiment, the sample-resuspension liquid comprises water. In addition, the sample-resuspension liquid may comprise a pH-adjusting component (e.g., an acid and/or a base), a buffer component (e.g., Butterfield's buffer), a surfactant, a chelating agent, and/or a metal ion.

The cell lysis reagent can be an effective amount of any cell lysis reagent known in the art for facilitating permeablization of a cell and/or causing the lysis of a cell (e.g., a eukaryotic cell, a prokaryotic cell, or both types of cells). Nonlimiting examples of cell lysis reagents include lysozyme, lysostaphin, TRITON X-100, deoxycholate, EDTA, and Proteinase K.

Reagents used in nucleic acid amplification reactions include, for example, a buffer, a metal salt (e.g., $MgCl_2$), a nucleic acid polymerase (e.g., Taq polymerase), a primer, and deoxyribonucleotide-triphosphates. Reagents used in an antigen-detection reaction include, for example, a buffer, an antibody (e.g., a primary antibody, a secondary antibody), a conjugated enzyme, an enzyme substrate, and a competitive antigen.

In any embodiment, the kit further can comprise a prefilter. The prefilter can have a nominal pore size that permits passage of microbial cells but retains particulate material (e.g., food particles, vegetable matter, sand, dirt) that is larger than microbial cells. In any embodiment, the prefilter may comprise a membrane filter. In any embodiment, the prefilter may have a nominal pore size of at least about 10 microns. In any embodiment, the prefilter may be dimensioned so that it can be inserted into the processing chamber (e.g., proximate the second end of the body of the apparatus).

In any embodiment, the kit further can comprise a culture device for growing and detecting a microorganism. The culture device can comprise a culture medium (e.g., a broth or semi-solid culture medium. Nonlimiting examples of suitable culture devices include tubes comprising broth media, Petri dishes, and a variety of culture devices sold under the trade name PETRIFILM (available from 3M Company; St. Paul, Minn.) or culture devices sold under the trade name SANITA-KUN (available from Chisso Corporation; Tokyo, Japan).

EXEMPLARY EMBODIMENTS

Embodiment A is an apparatus, comprising:
a body comprising a first end and a second end opposite the first end, the body comprising:
a processing chamber comprising an opening proximate the first end;
a first reservoir in selective fluid communication with the processing chamber via a first fluid pathway;
a second reservoir in selective fluid communication with the processing chamber via a second fluid pathway;
a filter through which the first fluid pathway and the second fluid pathway pass, the filter having a first side oriented in the fluid pathways toward the processing chamber and a second side opposite the first side;
a first one-way valve disposed in the first fluid pathway between the filter and the first reservoir, the first one-way valve providing selective fluid communication between the processing chamber and the first reservoir; and
a second one-way valve disposed in the second fluid pathway between the filter and the second reservoir, the second one-way valve providing selective fluid communication between the processing chamber and the second reservoir.

Embodiment B is the apparatus of Embodiment A, further comprising a plunger, wherein the processing chamber is shaped and dimensioned to operatively receive the plunger.

Embodiment C is the apparatus of Embodiment B, wherein the first one-way valve substantially prevents liquid flow from the processing chamber to the first reservoir and the second one-way valve substantially permits liquid flow from the processing chamber to the second reservoir.

Embodiment D is the apparatus of Embodiment A or Embodiment B, wherein the first one-way valve substantially permits liquid flow from the first reservoir to the processing chamber and the second one-way valve substantially prevents liquid flow from the second reservoir to the processing chamber.

Embodiment E is the apparatus of any one of the preceding Embodiments, wherein the first one-way valve comprises a pressure-actuated, one-way valve.

Embodiment F is the apparatus of any one of the preceding Embodiments, wherein the second one-way valve comprises a pressure-actuated, one-way valve.

Embodiment G is the apparatus of any one of the preceding Embodiments, wherein the filter is configured to substantially prevent the passage of biological cells from the processing chamber to the second reservoir.

Embodiment H is the apparatus of any one of the preceding Embodiments, wherein the filter is configured to substantially prevent the passage of cell concentration agents from the processing chamber to the second reservoir.

Embodiment I is the apparatus of any one of the preceding Embodiments, further comprising a first reservoir vent.

Embodiment J is the apparatus of any one of the preceding Embodiments, further comprising a second reservoir vent.

Embodiment K is the apparatus of any one of the preceding Embodiments, wherein the body further comprises a first visual indicium to indicate a first predetermined volume.

Embodiment L is the apparatus of Embodiment K, wherein the body comprises a second visual indicium to indicate a second predetermined volume.

Embodiment M is the apparatus of Embodiment K or Embodiment L, wherein the first and/or second visual indicium indicates a predetermined volume in the processing chamber.

Embodiment N is the apparatus of Embodiment K or Embodiment L, wherein the first and/or second visual indicium indicates a predetermined volume in the first reservoir or the second reservoir.

Embodiment O is the apparatus of any one of the preceding Embodiments, wherein the processing chamber defines a first operational volume, wherein the first reservoir defines a second operational volume that is less than or equal to the first operational volume.

Embodiment P is the apparatus of any one of Embodiments A through O, wherein the processing chamber defines a first operational volume, wherein the first reservoir defines a second operational volume that is greater than the first operational volume.

Embodiment Q is the apparatus of any one of the preceding Embodiments, wherein the processing chamber defines a first operational volume, wherein the second reservoir defines a third operational volume that is greater than or equal to the first operational volume.

Embodiment R is the apparatus of any one of the preceding Embodiments, further comprising a water-absorbent material disposed in the second reservoir.

Embodiment S is an apparatus, comprising:
a body comprising a first end and a second end opposite the first end, the body comprising
a plurality of liquid-sample processing modules including a first module and a second module, wherein each module of the plurality of modules comprises:
a processing chamber comprising an opening proximate the first end;
a first reservoir in selective fluid communication with the processing chamber via a first fluid pathway;
a second reservoir in selective fluid communication with the processing chamber via a second fluid pathway;
a filter through which the first fluid pathway and the second fluid pathway pass, the filter having a first side oriented in the fluid pathways toward the processing chamber and a second side opposite the first side;
a first one-way valve disposed in the first fluid pathway between the filter and the first reservoir, the first one-way valve providing selective fluid communication between the processing chamber and the first reservoir; and
a second one-way valve disposed in the second fluid pathway between the filter and the second reservoir, the second one-way valve providing selective fluid communication between the processing chamber and the second reservoir;

wherein the first module is coupled to the second module.

Embodiment T is the apparatus of Embodiment S, wherein the first module is detachably coupled to the second module.

Embodiment U is the apparatus of Embodiment S or T, further comprising a plunger, wherein at least one of the processing chambers is shaped and dimensioned to operatively receive the plunger.

Embodiment V is the apparatus of any one of Embodiments S through U, wherein at least one of the first one-way valve comprises a pressure-actuated, one-way valve.

Embodiment W is the apparatus of any one of Embodiments S through V, wherein at least one of the second one-way valve comprises a pressure-actuated, one-way valve.

Embodiment X is the apparatus of any one of Embodiments S through W, wherein at least one filter is configured to substantially prevent the passage of biological cells from the processing chamber to the second reservoir.

Embodiment Y is the apparatus of any one of Embodiments S through X, wherein at least one filter is configured to substantially prevent the passage of cell concentration agents from the processing chamber to the second reservoir.

Embodiment Z is the apparatus of any one of Embodiments S through Y, further comprising at least one first reservoir vent.

Embodiment AA is the apparatus of any one of Embodiments S through Z, further comprising at least one second reservoir vent.

Embodiment BB is the apparatus of any one of Embodiments S through AA, wherein the body further comprises a first visual indicium to indicate a first predetermined volume.

Embodiment CC is the apparatus of any one of Embodiments S through BB, wherein the body comprises a second visual indicium to indicate a second predetermined volume.

Embodiment DD is the apparatus of Embodiment BB or Embodiment CC, wherein the first and/or second visual indicium indicates a predetermined volume in the processing chamber.

Embodiment EE is the apparatus of Embodiment BB or Embodiment CC, wherein the first and/or second visual indicium indicates a predetermined volume in the first reservoir or the second reservoir.

Embodiment FF is the apparatus of any one of Embodiments S through EE, wherein at least one processing chamber defines a first operational volume, wherein the first reservoir in selective fluid communication therewith defines a second operational volume that is less than or equal to the first operational volume.

Embodiment GG is the apparatus of any one of Embodiments S through FF, wherein at least one processing chamber defines a first operational volume, wherein the first reservoir in selective fluid communication therewith defines a second operational volume that is greater than or equal to the first operational volume.

Embodiment HH is the apparatus of any one of Embodiments S through GG, wherein at least one processing chamber defines a first operational volume, wherein the second reservoir in selective fluid communication therewith defines a third operational volume that is greater than or equal to the first operational volume.

Embodiment II is the apparatus of any one of Embodiments S through HH, further comprising a water-absorbent material disposed in at least one second reservoir.

Embodiment JJ is an apparatus, comprising:
a body comprising a first end and a second end opposite the first end, the body comprising:
  a plurality of processing chambers comprising a first processing chamber and a second processing chamber, each processing chamber comprising an opening proximate the first end;
  a first reservoir in selective fluid communication with the first processing chamber via a first fluid pathway;
  a second reservoir in selective fluid communication with the first processing chamber via a second fluid pathway and in selective fluid communication with the second processing chamber via a third fluid pathway;
  a first filter disposed in the body between at least a portion of the processing chamber and the second reservoir;
    wherein the first fluid pathway and the second fluid pathway pass through the first filter;
    wherein the first filter has a first surface oriented in the first and second fluid pathways toward the first processing chamber;
  a second filter disposed in the body between at least a portion of the processing chamber and the second reservoir;
    wherein the third pathway passes through the second filter;
    wherein the first filter has a first surface oriented in the third fluid pathway;
  a first one-way valve disposed between the first filter and the first reservoir, the first one-way valve providing selective fluid communication between the first processing chamber and the first reservoir; and
  a second one-way valve disposed in the second fluid pathway between the first filter and the second reservoir, the second one-way valve providing selective fluid communication between the first processing chamber and the second reservoir; and
  a third one-way valve disposed in the third fluid pathway between the second filter and the first reservoir, the third one-way valve providing selective fluid communication between the second processing chamber and the first reservoir.

Embodiment KK is the apparatus of Embodiment JJ, wherein the apparatus comprises a fourth one-way valve disposed between the second filter and the second reservoir, the fourth one-way valve providing selective fluid communication between the second processing chamber and the second reservoir.

Embodiment LL is the apparatus of Embodiment JJ or Embodiment KK, wherein at least one of the first one-way valve, the second one-way valve, the third one-way valve or the fourth one-way valve comprises a pressure-actuated, one-way valve.

Embodiment MM is the apparatus of any one of Embodiments JJ through LL, wherein at least one filter is configured to substantially prevent the passage of biological cells from the processing chamber to the second reservoir.

Embodiment NN is the apparatus of Embodiments JJ through MM, wherein at least one filter is configured to substantially prevent the passage of cell concentration agents from the processing chamber to the second reservoir.

Embodiment OO is the apparatus of Embodiments JJ through NN, further comprising at least one first reservoir vent.

Embodiment PP is the apparatus of Embodiments JJ through OO, further comprising at least one second reservoir vent.

Embodiment QQ is the apparatus of Embodiments JJ through PP, wherein the body further comprises a first visual indicium to indicate a first predetermined volume.

Embodiment RR is the apparatus of Embodiments JJ through QQ, wherein the body comprises a second visual indicium to indicate a second predetermined volume.

Embodiment SS is the apparatus of Embodiment QQ or Embodiment RR, wherein the first and/or second visual indicium indicates a predetermined volume in the processing chamber.

Embodiment TT is the apparatus of Embodiments QQ or Embodiment RR, wherein the first and/or second visual indicium indicates a predetermined volume in the first reservoir or the second reservoir.

Embodiment UU is the apparatus of Embodiments JJ through TT, wherein at least one processing chamber defines a first operational volume, wherein the first reservoir in selective fluid communication therewith defines a second operational volume that is less than or equal to the first operational volume.

Embodiment VV is the apparatus of Embodiments JJ through UU, wherein at least one processing chamber defines a first operational volume, wherein the first reservoir in selective fluid communication therewith defines a second operational volume that is greater than or equal to the first operational volume.

Embodiment WW is the apparatus of Embodiments JJ through VV, wherein at least one processing chamber defines a first operational volume, wherein the second reservoir in selective fluid communication therewith defines a third operational volume that is greater than or equal to the first operational volume.

Embodiment XX is the apparatus of Embodiments JJ through WW, further comprising a water-absorbent material disposed in at least one second reservoir.

Embodiment YY is a method, comprising:
placing a sample comprising a liquid into the processing chamber of the apparatus of any one of the preceding claims;
urging at least a portion of the liquid out of the processing chamber through the filter;
after urging the at least a portion of the liquid through the filter, urging a first portion of a back-flush liquid from the first reservoir through the filter and into the process chamber to form a first processed sample; and
analyzing at least a portion of the sample to detect an indication of a microorganism, wherein analyzing at least a portion of the sample comprises analyzing at least a portion of the first processed sample.

Embodiment ZZ is the method of Embodiment YY, wherein urging at least a portion of the liquid through the filter comprises inserting a plunger into the processing chamber and using the plunger to generate a positive pressure in the processing chamber.

Embodiment AAA is the method of Embodiment ZZ, wherein urging a first portion of the back-flush liquid through the filter from the second side comprises using the plunger to generate a negative pressure in the processing chamber.

Embodiment BBB is the method of any one of Embodiments YY through AAA, wherein placing a sample comprising a liquid into the processing chamber comprises placing a first predetermined volume of liquid into the processing chamber, wherein forming a first processed sample comprises forming a first processed sample have a second predetermined volume, wherein the second predetermined volume is less than or equal to the first predetermined volume.

Embodiment CCC is the method of Embodiment BBB, wherein forming a first processed sample having a second predetermined volume comprises using a visible indicium on the processing chamber or the first reservoir to define the second predetermined volume.

Embodiment DDD is the method of any one of Embodiments YY through CCC, further comprising:
after forming the first processed sample, urging at least a portion of the first processed sample out of the processing chamber through the filter;
urging a second portion of back-flush liquid from the first reservoir through the filter and into the process chamber to form a second processed sample;
wherein analyzing at least a portion of the sample to detect an indication of a microorganism comprises analyzing at least a portion of the second processed sample.

Embodiment EEE is the method of Embodiment DDD, wherein placing a sample comprising a liquid into the processing chamber comprises placing a first predetermined volume of sample into the processing chamber, wherein forming a second processed sample comprises forming a second processed sample having a third predetermined volume, wherein the third predetermined volume is smaller than the first predetermined volume.

Embodiment FFF is the method of Embodiment EEE, wherein forming a second processed sample having a third predetermined volume comprises using a visible indicium on the processing chamber or the first reservoir to define the third predetermined volume.

Embodiment GGG is the method of any one of Embodiments YY through FFF, wherein analyzing at least a portion of the first processed sample or analyzing at least a portion of the second processed sample comprises analyzing the portion of the first processed sample or second processed sample to detect an antigen, a nucleic acid, an enzyme activity, or a viable microorganism.

Embodiment HHH is the method of any one of Embodiments YY through FFF, further comprising:
after urging at least a portion of the liquid through the filter, adjusting the temperature of the processing chamber to about 95-100° C.

Embodiment III is the method of Embodiment HHH, wherein adjusting the temperature of the processing chamber comprises placing the apparatus in a heated device.

Embodiment JJJ is a kit comprising the apparatus of any one of Embodiments A through XX.

Embodiment KKK is the kit of Embodiment JJJ, further comprising a reagent selected from the group consisting of a sample back-flush liquid, a cell-lysis reagent, a reagent used in a nucleic acid amplification reaction, and a reagent used in an antigen detection reaction.

Embodiment LLL is the kit of Embodiment JJJ or Embodiment KKK, further comprising a prefilter.

Embodiment MMM is the kit of any one of Embodiments JJJ through LLL, further comprising a culture device.

Objects and advantages of this invention are further illustrated by the following examples, but the particular materials and amounts thereof recited in these examples, as well as other conditions and details, should not be construed to unduly limit this invention.

EXAMPLES

Sample Preparation Apparatus

An apparatus consisting of an individual sample-processing module 4105 of the apparatus 4000 described in FIG. 8 was fabricated from Accura® 60 plastic (3D Systems, Rock Hill, S.C.) using a stereolithographic process. The processing chamber was about 35 mm in height. The first reservoir and second reservoir were each about 30 mm in height. The processing chamber was shaped as a cylinder (5.7 mm diameter) and had an internal volume of about 0.89 mL. The first reservoir had an internal volume of about 1.2 mL and the second reservoir had an internal volume of about 1.4 mL.

The circular filter (8 mm diameter) was die cut from a Versapor® acrylic copolymer membrane disc filter having a pore size of 0.8 microns and a nominal thickness of 94 microns (part number 66404, Pall Corporation, Port Washington, N.Y.). The filter was positioned at the bottom of the processing chamber and secured in the processing chamber with elastic sealing rings. The two one-way Belleville-type minivalves (4.0 mm in diameter, part number UM040.002) were obtained from Minivalve Incorporated, Cleveland, Ohio. The plunger was fabricated from Accura® 60 plastic and dimensioned to have a tight but movable fit with the interior of the processing chamber. The tip of the plunger was fabricated from conformable TangoPlus resin (Stratasys Corporation, Minneapolis, Minn.) using a stereolithographic process. The tip portion was attached to the plunger shaft using a friction fit. The movement of liquid was controlled by the operation of the plunger mated with the processing chamber. The minivalves were oriented to allow for unidirectional liquid flow from the first reservoir to the processing chamber and unidirectional liquid flow from the processing chamber to the second reservoir. When the plunger was depressed into the processing chamber liquid moved from the processing chamber to the second reservoir. When the plunger was withdrawn from the processing chamber to an extended position the buffer reagent entered the processing chamber from the first reservoir.

Example 1

A *Salmonella enterica* sample (ATCC 14028) was obtained from a frozen stock reference standard that was subcultured and then serially diluted with buffered peptone water broth (BPW-ISO, 3M Corporation, St. Paul, Minn.) to a concentration of $1 \times 10^3$ cfu/mL. The concentration was confirmed using a 3M PETRIFILM Aerobic Count Plate (catalog number 6400, 3M Corporation). An aliquot of the *Salmonella* culture sample (250 µL) was added by pipette to the processing chamber of the Sample Preparation Apparatus through the port (i.e., the port 125' of FIG. 8). Next, 500 µL of Butterfield's Buffer Solution (3M Corporation) was added by pipette to the first reservoir of the assembly. The culture sample was filtered by depressing the plunger so that the sample passed through the filter element with the filtrate being transferred to the second reservoir. The filter was washed with buffer regent by pulling back on the plunger so that approximately 200 µL of the buffer reagent back-flushed the filter and entered the processing chamber. The plunger was then depressed to move the buffer reagent through the filter with the filtrate entering the second reservoir. The wash procedure was repeated with a second 200 µL portion of the buffer reagent. The plunger was then pulled back to a stopping position located beyond the opening of the port to allow approximately 75 µL of buffer reagent to back-flush the filter and enter the processing chamber.

A pipette was inserted through the port and used to transfer 20 µL of the buffer reagent containing resuspended cells to a vial containing 0.98 mL of Butterfield's Buffer Solution (3M Corporation). The diluted sample (1 mL) was applied by pipette to the center of the growth region of a 3M PETRIFILM Enterobacteriaceae Count Plate (catalog number 6420, 3M Corporation). The sample was uniformly spread using the spreading device provided by the manufacturer (3M). The inoculated plate was incubated at 37° C. for 24 hours. An indicator dye in the plate allowed for visual counting of colonies. Red colored colonies having a yellow colored acid zone and at least one associated gas bubble were counted. A total of three plates were prepared and analyzed. The mean colony count per plate was 87.

Reference Example 1

The *Salmonella enterica* sample ($1 \times 10^3$ cfu/mL) prepared in Example 1 was used. The sample was not processed using the Sample Preparation Apparatus of Example 1. A 20 µL aliquot of the *Salmonella enterica* sample was added to a vial containing 0.98 mL of Butterfield's Buffer. The diluted sample (1 mL) was applied by pipette to the center of the growth region of a 3M PETRIFILM Enterobacteriaceae Count Plate (catalog number 6420, 3M Corporation). The sample was uniformly spread using the spreading device provided by the manufacturer (3M). An indicator dye in the plate allowed for visual counting of colonies. Red colored colonies having a yellow colored acid zone and at least one associated gas bubble were counted. A total of three plates were prepared and analyzed. The mean colony count per plate was 29.

The complete disclosure of all patents, patent applications, and publications, and electronically available material cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

Various modifications may be made without departing from the spirit and scope of the invention. These and other embodiments are within the scope of the following claims.

The invention claimed is:

1. An apparatus, comprising:
  a body comprising a first end and a second end opposite the first end, the body comprising:
    a plurality of processing chambers comprising a first processing chamber and a second processing chamber, each processing chamber comprising an opening proximate the first end;
    a first reservoir disposed in selective fluid communication with the first processing chamber via a first fluid pathway;
    a second reservoir disposed in selective fluid communication with the first processing chamber via a second fluid pathway and in selective fluid communication with the second processing chamber via a third fluid pathway;

a first filter disposed in the body between at least a portion of the first processing chamber and the second reservoir;
  wherein the first fluid pathway and the second fluid pathway pass through the first filter;
  wherein the first filter has a first surface oriented in the first and second fluid pathways toward the first processing chamber;
a second filter disposed in the body between at least a portion of the second processing chamber and the second reservoir;
  wherein the third pathway passes through the second filter;
  wherein the first filter has a first surface oriented in the third fluid pathway;
a first one-way valve disposed between the first filter and the first reservoir, the first one-way valve providing selective fluid communication between the first processing chamber and the first reservoir; and
a second one-way valve disposed in the second fluid pathway between the first filter and the second reservoir, the second one-way valve providing selective fluid communication between the first processing chamber and the second reservoir; and
a third one-way valve disposed in the third fluid pathway between the second filter and the first reservoir, the third one-way valve providing selective fluid communication between the second processing chamber and the first reservoir.

2. The apparatus of claim 1, wherein the apparatus comprises a fourth one-way valve disposed between the second filter and the second reservoir, the fourth one-way valve providing selective fluid communication between the second processing chamber and the second reservoir.

3. The apparatus of claim 1, wherein at least one of the first filter and second filter is configured to prevent the passage of biological cells or cell concentration agents from at least one of the first and second the processing chambers to the second reservoir.

4. The apparatus of claim 1, further comprising a plunger in at least one of the first and second processing chambers.

5. The apparatus of claim 1, wherein the first reservoir comprises a vent.

6. The apparatus of claim 1, wherein the second reservoir comprises a vent.

7. The apparatus of claim 1, wherein the first processing chamber defines a first operational volume, wherein the first reservoir defines a second operational volume that is greater than the first operational volume.

8. The apparatus of claim 1, wherein the first processing chamber defines a first operational volume, wherein the second reservoir defines a third volume that is greater than or equal to the first operational volume.

* * * * *

UNITED STATES PATENT AND TRADEMARK OFFICE
CERTIFICATE OF CORRECTION

| | |
|---|---|
| PATENT NO. | : 10,363,557 B2 |
| APPLICATION NO. | : 16/124715 |
| DATED | : July 30, 2019 |
| INVENTOR(S) | : Jon Kirschhoffer et al. |

Page 1 of 1

It is certified that error appears in the above-identified patent and that said Letters Patent is hereby corrected as shown below:

In the Specification

Column 6, Line 45, delete "may be" and insert -- may --

Column 24, Line 49-50, delete "permeablization" and insert -- permeabilization --

Column 26, Line 45, delete "comprising" and insert -- comprising: --

In the Claims

Column 34, Line 11, after "second" delete "the"

Signed and Sealed this
Fifth Day of May, 2020

Andrei Iancu
*Director of the United States Patent and Trademark Office*